(12) United States Patent
Grim et al.

(10) Patent No.: US 10,786,224 B2
(45) Date of Patent: Sep. 29, 2020

(54) BIOPSY DEVICES AND METHODS OF USE THEREOF

(71) Applicant: COVIDIEN LP, Mansfield, MA (US)

(72) Inventors: Kasey A. Grim, Boulder, CO (US); Joe D. Sartor, Longmont, CO (US); Graham J. Carson, Louisville, CO (US); Jason S. F. McGrath, Broomfield, CO (US); Joan Ortega Alcaide, Barcelona (ES); Suchit A. Madan, Longmont, CO (US)

(73) Assignee: Covidien LP, Mansfield, MA (US)

( * ) Notice: Subject to any disclaimer, the term of this patent is extended or adjusted under 35 U.S.C. 154(b) by 584 days.

(21) Appl. No.: 15/490,963

(22) Filed: Apr. 19, 2017

(65) Prior Publication Data

US 2017/0303889 A1   Oct. 26, 2017

Related U.S. Application Data

(60) Provisional application No. 62/325,788, filed on Apr. 21, 2016.

(51) Int. Cl.
*A61B 8/08* (2006.01)
*A61B 10/02* (2006.01)
(Continued)

(52) U.S. Cl.
CPC ............ *A61B 8/0841* (2013.01); *A61B 8/445* (2013.01); *A61B 8/4444* (2013.01); *A61B 8/462* (2013.01);
(Continued)

(58) Field of Classification Search
CPC ..... A61B 8/0841; A61B 8/4444; A61B 8/462; A61B 8/445; A61B 10/0283;
(Continued)

(56) References Cited

U.S. PATENT DOCUMENTS

| 4,108,165 A * | 8/1978 | Kopp ................... A61B 8/0833 600/461 |
| 4,321,551 A | 3/1982 | Bleil et al. |

(Continued)

FOREIGN PATENT DOCUMENTS

| CN | 203001001 U | 6/2013 |
| EP | 1932481 A1 | 6/2008 |

(Continued)

OTHER PUBLICATIONS

International Search Report and Written Opinion, dated Jun. 21, 2017, corresponding to International Application No. PCT/US2017/028498; 11 total pages.

(Continued)

*Primary Examiner* — Pascal M Bui Pho
*Assistant Examiner* — Sean D Mattson
(74) *Attorney, Agent, or Firm* — Carter, DeLuca & Farrell LLP

(57) ABSTRACT

A biopsy device includes an ultrasonic probe, a display, an actuator, and a needle assembly. The display is associated with the ultrasonic probe, and the ultrasonic probe is configured to send a signal to the display to generate an image on the display. The needle assembly is coupled to the actuator and is at least partially disposed within a channel defined in the ultrasonic probe. The actuator is configured to move the needle assembly in a distal direction relative to the ultrasonic probe and through the channel of the ultrasonic probe from a retracted position to a deployed position.

20 Claims, 32 Drawing Sheets

(51) Int. Cl.
*A61B 8/00* (2006.01)
*A61B 17/34* (2006.01)

(52) U.S. Cl.
CPC ...... *A61B 10/0266* (2013.01); *A61B 10/0283* (2013.01); *A61B 17/3403* (2013.01); *A61B 2010/0208* (2013.01); *A61B 2017/3413* (2013.01)

(58) Field of Classification Search
CPC ............ A61B 10/0266; A61B 17/3403; A61B 2010/0208; A61B 2017/3413; A61B 8/4494; A61B 8/4422; A61B 8/4411; A61B 8/4281; A61B 8/429
See application file for complete search history.

(56) References Cited

U.S. PATENT DOCUMENTS

| | | | |
|---|---|---|---|
| 4,671,292 A * | 6/1987 | Matzuk | A61B 8/0833 600/445 |
| 5,320,110 A | 6/1994 | Wang | |
| 5,526,822 A | 6/1996 | Burbank et al. | |
| 5,598,269 A | 1/1997 | Kitaevich et al. | |
| 5,660,185 A | 8/1997 | Shmulewitz et al. | |
| 5,751,869 A | 5/1998 | Li et al. | |
| 5,810,541 A | 9/1998 | Casey et al. | |
| 5,810,841 A | 9/1998 | McNeirney et al. | |
| 5,855,554 A | 1/1999 | Schneider et al. | |
| 5,976,092 A | 11/1999 | Chinn | |
| 6,007,497 A | 12/1999 | Huitema | |
| 6,063,031 A | 5/2000 | Cundari et al. | |
| 6,069,748 A | 5/2000 | Bietry | |
| 6,086,544 A | 7/2000 | Hibner et al. | |
| 6,102,866 A | 8/2000 | Nields et al. | |
| 6,203,498 B1 | 3/2001 | Bunce et al. | |
| 6,273,862 B1 | 8/2001 | Privitera et al. | |
| 6,364,839 B1 | 4/2002 | Little et al. | |
| D461,895 S | 8/2002 | Barnes et al. | |
| 6,428,487 B1 | 8/2002 | Burdorff et al. | |
| 6,471,651 B1 | 10/2002 | Hwang et al. | |
| 6,582,368 B2 | 6/2003 | Holdaway et al. | |
| 6,605,095 B2 | 8/2003 | Grossman | |
| 6,688,758 B2 | 2/2004 | Thibault | |
| 6,689,067 B2 | 2/2004 | Sauer et al. | |
| 6,692,200 B2 | 2/2004 | Peterson | |
| 6,702,749 B2 | 3/2004 | Paladini et al. | |
| 6,752,768 B2 | 6/2004 | Burdorff et al. | |
| 6,945,942 B2 | 9/2005 | Van Bladel et al. | |
| 7,024,791 B2 | 4/2006 | Marshall et al. | |
| 7,031,367 B2 | 4/2006 | Marshall et al. | |
| 7,041,058 B2 | 5/2006 | Piehler | |
| 7,244,234 B2 * | 7/2007 | Ridley | A61B 8/0833 600/459 |
| 7,269,907 B2 | 9/2007 | Levine et al. | |
| 7,303,530 B2 | 12/2007 | Barnes et al. | |
| 7,310,887 B2 | 12/2007 | Nash et al. | |
| 7,367,945 B2 | 5/2008 | Dasgupta et al. | |
| 7,416,533 B2 | 8/2008 | Gellman et al. | |
| 7,465,278 B2 * | 12/2008 | Cicenas | A61B 10/0275 600/565 |
| 7,722,549 B2 | 5/2010 | Nakao | |
| 7,858,038 B2 | 12/2010 | Andreyko et al. | |
| 8,162,852 B2 | 4/2012 | Norris | |
| 2002/0082518 A1 * | 6/2002 | Weiss | A61B 10/0283 600/566 |
| 2002/0173719 A1 | 11/2002 | Zhao et al. | |
| 2003/0014010 A1 | 1/2003 | Carpenter et al. | |
| 2003/0069502 A1 | 4/2003 | Makin et al. | |
| 2003/0199753 A1 | 10/2003 | Hibner et al. | |
| 2003/0199754 A1 | 10/2003 | Hibner et al. | |
| 2003/0199785 A1 | 10/2003 | Hibner et al. | |
| 2004/0034280 A1 | 2/2004 | Privitera et al. | |
| 2004/0077972 A1 | 4/2004 | Tsonton et al. | |
| 2004/0106934 A1 | 6/2004 | Grossman | |
| 2004/0249278 A1 | 12/2004 | Krause | |
| 2004/0267121 A1 | 12/2004 | Sarvazyan et al. | |
| 2005/0065453 A1 | 3/2005 | Shabaz et al. | |
| 2005/0131291 A1 | 6/2005 | Floyd et al. | |
| 2006/0144548 A1 | 7/2006 | Beckman et al. | |
| 2006/0200041 A1 | 9/2006 | Weikel et al. | |
| 2007/0049822 A1 | 3/2007 | Bunce et al. | |
| 2007/0149878 A1 | 6/2007 | Hankins | |
| 2007/0167736 A1 | 7/2007 | Dietz et al. | |
| 2007/0232953 A1 | 10/2007 | Dietz et al. | |
| 2008/0015429 A1 | 1/2008 | Tsonton et al. | |
| 2008/0146915 A1 | 6/2008 | McMorrow | |
| 2009/0118641 A1 | 5/2009 | Van Dam et al. | |
| 2009/0326412 A1 | 12/2009 | Pakter | |
| 2010/0174185 A1 | 7/2010 | Wang et al. | |
| 2011/0087132 A1 | 4/2011 | DeFreitas et al. | |
| 2011/0125055 A1 | 5/2011 | Privitera et al. | |
| 2011/0319759 A1 | 12/2011 | Liu et al. | |
| 2014/0257110 A1 * | 9/2014 | Chang | A61B 8/0841 600/461 |
| 2016/0007956 A1 * | 1/2016 | Mauldin, Jr. | A61B 8/0841 600/443 |

FOREIGN PATENT DOCUMENTS

| | | |
|---|---|---|
| WO | 2008120137 A1 | 10/2008 |
| WO | 2009067740 A1 | 6/2009 |
| WO | 2015193917 A2 | 12/2015 |

OTHER PUBLICATIONS

Extended European Search Report for application No. 17786601.9 dated Apr. 8, 2020.

* cited by examiner

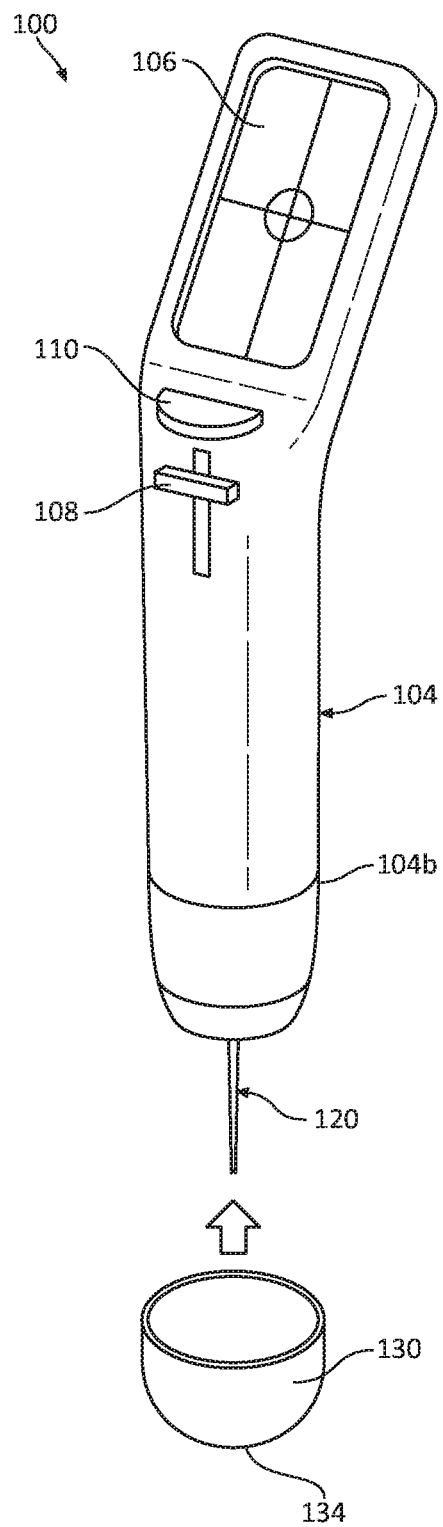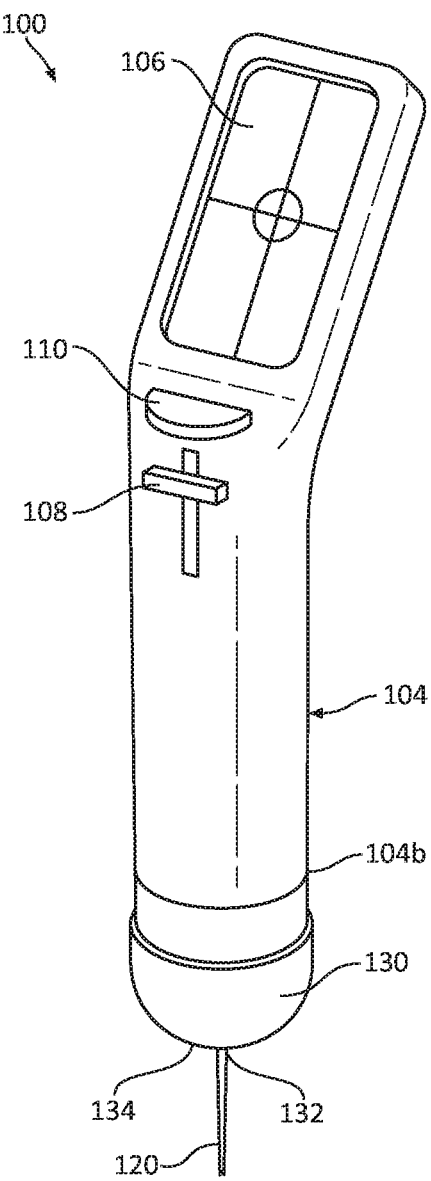
FIG. 2A
FIG. 2B

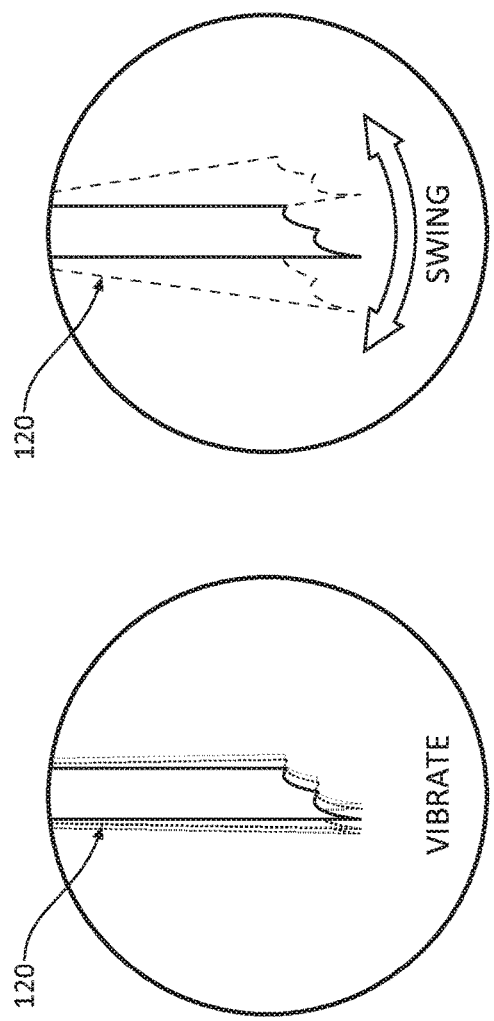
FIG. 6A
FIG. 6B
FIG. 6C
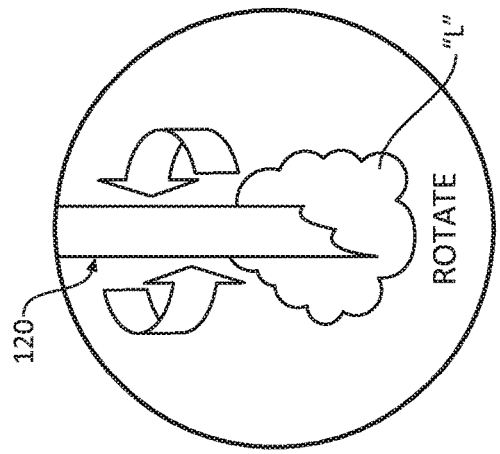
FIG. 6E
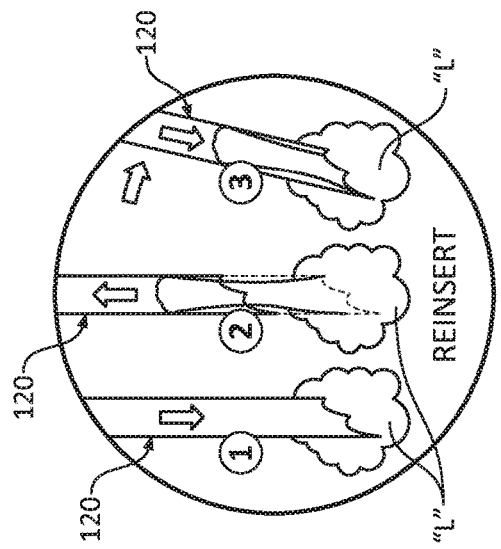
FIG. 6D
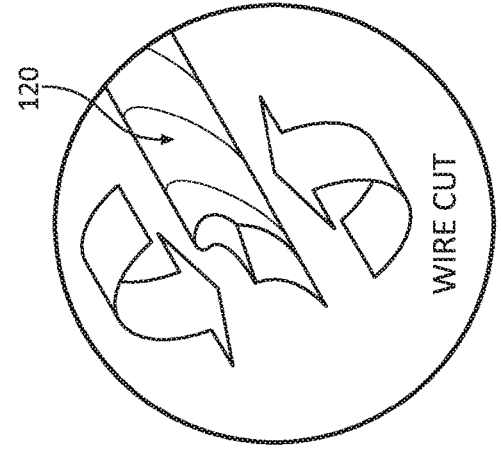

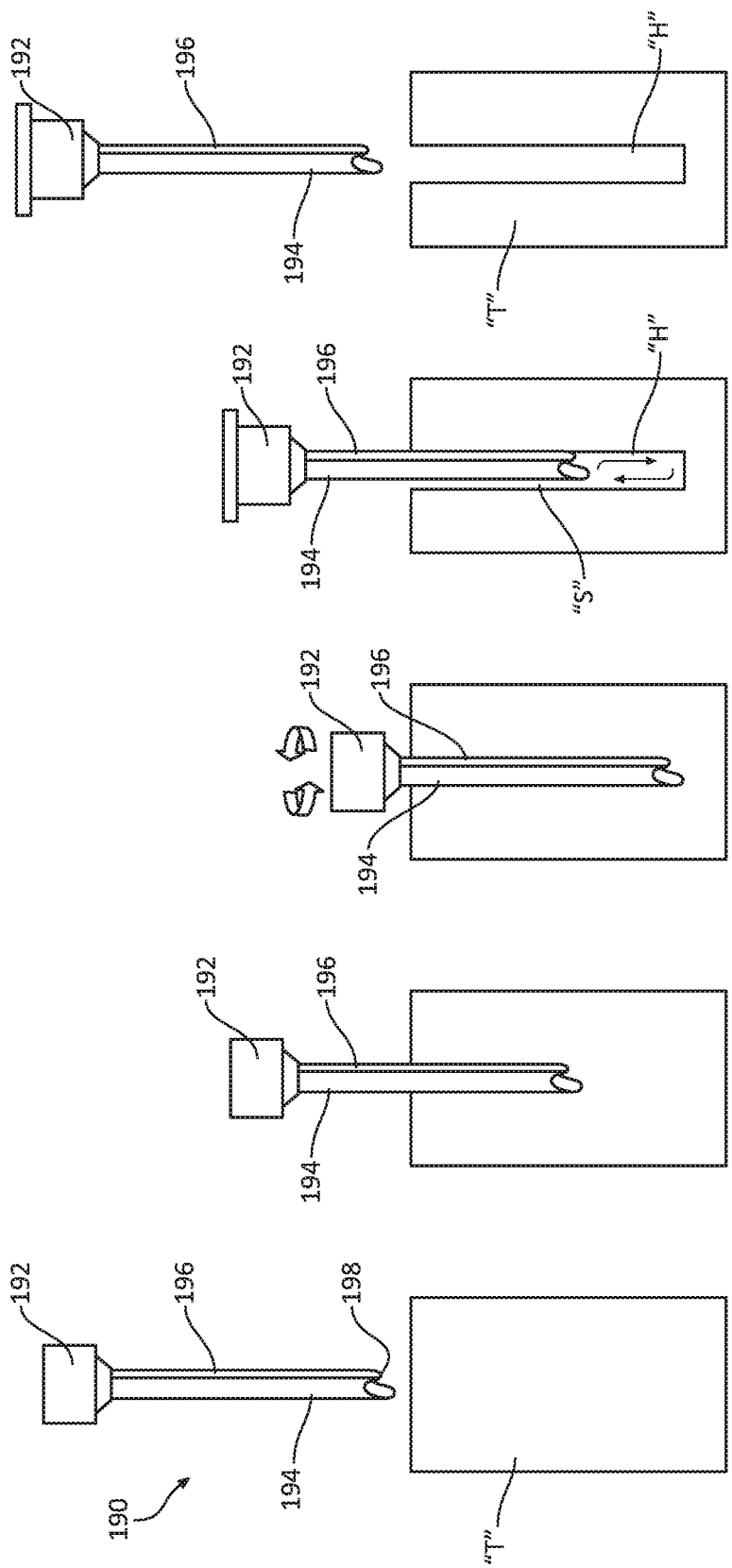

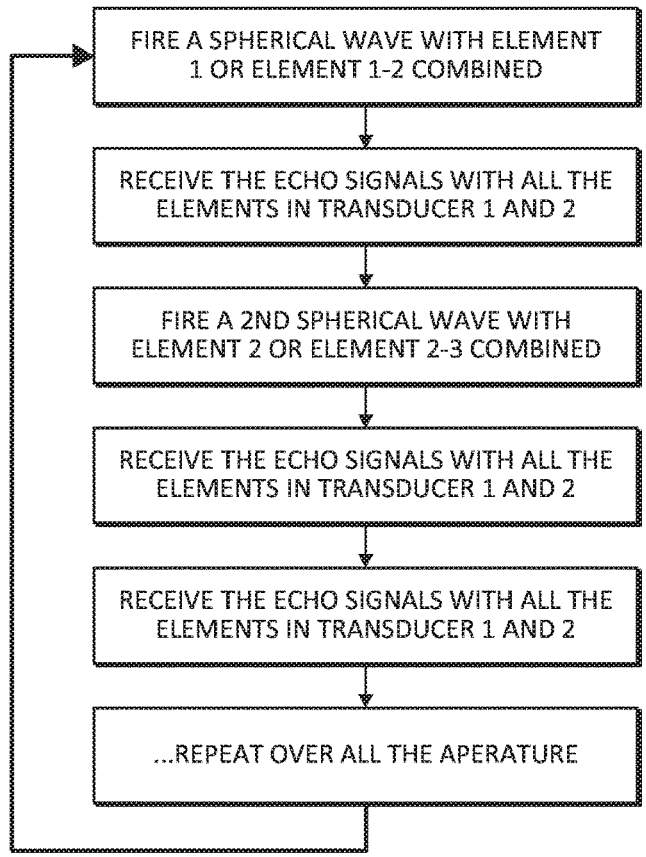
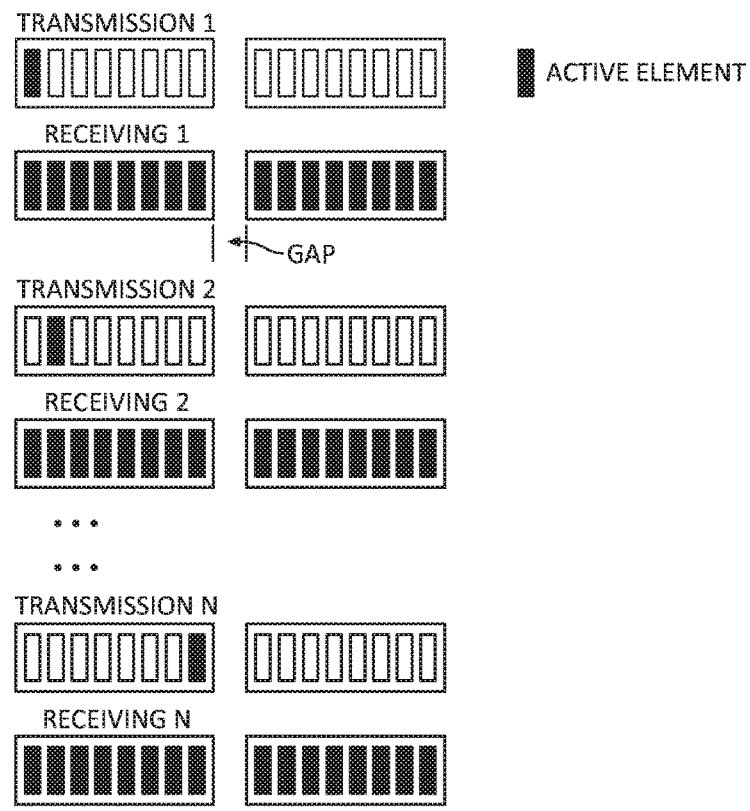
FIG. 19

BIOPSY DEVICES AND METHODS OF USE THEREOF

BACKGROUND

Technical Field

The present disclosure relates to biopsy sampling and, more particularly, to biopsy devices, biopsy systems, and methods for navigating a biopsy device to a target location and obtaining a tissue sample using the biopsy device.

Description of Related Art

To successfully treat cancer, it is critical to diagnose cancer at an early stage. Various methods are used to identify the existence of abnormalities in tissue prior to a patient being symptomatic. For example, women regularly go for prophylactic mammograms to determine whether there are any early stage tumors developing in their breast tissue. Although mammography is effective at identifying whether a tumor is present, mammography is not capable of differentiating between benign and malignant tumors. Accordingly, upon identifying an abnormality in the tissue, the status of the abnormality needs to be determined using an additional diagnostic technique.

One method to verify whether a tissue is cancerous is to obtain a tissue sample for histological examination through a biopsy of the tissue (e.g., breast tissue) near the lesion. There are a number of devices and methods for performing a biopsy. In some instances, a tumor may be identified using manual palpation of the breast tissue and then a biopsy needle may be positioned over the identified tumor to take a sample of tissue. Another method involves holding an ultrasound probe in one hand while holding the biopsy needle with a second hand and guiding the biopsy needle along the image plane of the ultrasound probe.

Proper placement of the biopsy needle in the target tissue is important for accurate breast cancer diagnosis. As already noted, traditional breast biopsy techniques involve blind, manual palpation of the lesion or the use of a separate imaging guidance system. Small lumps of cancerous tissue may be mobile, and therefore may be pushed away by the biopsy device during insertion of the biopsy device into the target tissue. Some tissue may be hard, and therefore may deflect the biopsy device during insertion into the target tissue, resulting in the clinician removing tissue samples from only a small portion of the side of the target tissue.

SUMMARY

Provided in accordance with the present disclosure is a biopsy device including an ultrasonic probe, a display, an actuator, and a needle assembly. The display is associated with the ultrasonic probe, and the ultrasonic probe is configured to send a signal to the display to generate an image on the display. The needle assembly is coupled to the actuator and is at least partially disposed within a channel defined in the ultrasonic probe. The actuator is configured to move the needle assembly in a distal direction relative to the ultrasonic probe and through the channel of the ultrasonic probe from a retracted position to a deployed position.

In some embodiments, the ultrasonic probe may be configured to capture images of the target lesion and the needle position at the extent of travel or at the instance the sample is captured within the needle. The biopsy device may include a processor for storing the image and transferring a memory and the needle assembly, or otherwise transmitting the image with reference, to the needle assembly specific ID.

The biopsy device is contemplated to have a sterile cover to prevent the ultrasonic probe from contacting the skin of the patient. The sterile cover may have a window for the ultrasonic sensor. The window may be composed of a silicone, plastic and/or gel material and may be ultrasonically conductive. The silicone or ultrasonically conductive material may have sufficient thickness to include a majority of a depth of a shadow formed by the gap or hole in the sensor through which the needle passes.

In embodiments, the needle assembly may be a selectively attachable cartridge that may be composed of a coring needle or a needle assembly with a notched core and a sliding sleeve. The needle may be safely positioned inside the cartridge preventing unintended contact that could result in a puncture to the user or loss of sterilization of the needle surface. The cartridge may have a unique ID that is traceable to the pathologic outcomes by transmitting the ID by electronic means to the handle processor or a connected patient record system.

In some methods, a verification image of the biopsy may be captured as proof that the needle successfully captured the tissue. The cartridge is extracted with the captured portion of tissue to a location for pathologic analysis along with the captured ultrasonic imaging confirming the biopsy location.

In most aspects of the present disclosure, the disclosed biopsy devices are designed to enable the user to target and execute a biopsy with a single hand. The second hand is free for manipulating the breast tissue to control the target location, and bunch or flatten the tissue as needed to achieve appropriate needle depth rather than adjusting the needle depth within the device.

In some embodiments, the ultrasonic probe may define a longitudinal axis therealong. The ultrasonic probe emits ultrasonic waves such that the movement of the needle assembly from the retracted position toward the deployed position aligns with the ultrasonic waves. The ultrasonic probe may be configured to send signals to the display corresponding to a position of a needle of the needle assembly to generate an image on the display of the position of the needle of the needle assembly.

It is contemplated that the needle assembly may include a hub and a needle extending distally from the hub. The actuator may be configured to rotate the needle about a longitudinal axis thereof after the needle assembly is moved from the retracted position to the deployed position.

It is envisioned that the needle assembly may include a body that defines a chamber therein, and a needle extending distally from the body. The biopsy device may further include a tube extending alongside the needle.

In some embodiments, the biopsy device may further include an adjustment mechanism movably coupled to the ultrasonic probe and configured to adjust and set a needle depth of the needle assembly such that an actuation of the actuator moves the needle assembly from the retracted position to the deployed position a longitudinal distance corresponding to the needle depth set by the adjustment mechanism.

It is contemplated that the ultrasonic probe may include a distal cap defining a central opening having a needle of the needle assembly extending therethrough. The distal cap may have a window for conducting ultrasound waves therethrough.

It is envisioned that the biopsy device may include a force sensor coupled to a distal end portion of the ultrasonic probe and extending distally beyond a distal end portion of the needle assembly when disposed in the retracted position. The ultrasonic probe may include an annular member extending distally from the distal end portion thereof. The force sensor may include a plurality of force sensors disposed in an annular array on the annular member.

In another aspect of the present disclosure, a method of performing a biopsy is provided. The method includes positioning a biopsy device in proximity to target tissue; generating an image of the target tissue on a display of the biopsy device using an ultrasonic probe of the biopsy device; aligning a needle of a needle assembly that is disposed within the ultrasonic probe with the target tissue using the image of the target tissue generated on the display; and deploying the needle of the needle assembly from the ultrasound probe into the target tissue, thereby capturing a tissue sample from the target tissue in the needle.

In some methods, aligning the needle with the target tissue may include moving the biopsy device relative to the target tissue into a position in which a projected needle pathway animated on the display is in line with the image of the target tissue on the display. Deploying the needle into the target tissue may include guiding the needle into the target tissue along the projected needle pathway.

The method may further include automatically capturing an image of the needle of the needle assembly with the tissue sample disposed therein.

The method may further include abutting a force sensor of the biopsy device with a tissue surface to determine a resistance of the target tissue prior to deploying the needle into the target tissue.

In some methods, a negative pressure may be applied to the needle assembly to draw the tissue sample into a containment chamber of the needle assembly. The negative pressure may be applied using hydraulics or a vacuum.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Various aspects and features of the present disclosure are described hereinbelow with references to the drawings, wherein:

FIG. 2A is a perspective view of the ultrasonic biopsy device of FIG. 1 and a cover;

FIG. 2B is a perspective view of the ultrasonic biopsy device of FIG. 1 illustrating the cover of FIG. 2 attached thereto;

FIGS. 6A-6E illustrate various methods of using the needle of FIG. 5A to extract a tissue sample;

FIGS. 12A-12E illustrate a method of extracting a tissue sample using yet another embodiment of a needle assembly;

FIG. 19 illustrates a scan sequence;

DETAILED DESCRIPTION

Biopsy devices, biopsy systems, and methods for navigating the biopsy devices to a target location and obtaining a tissue sample using the biopsy device are provided in accordance with the present disclosure and described in detailed below. In one embodiment, the biopsy device includes a handle assembly in the form of an ultrasonic probe, and a needle coupled to the handle assembly and configured for penetrating and extracting tissue from a lesion. The handle assembly has a display or screen for illustrating both a needle tip of the needle and the target tissue such that the needle can be accurately navigated into the targeted portion of the lesion.

Detailed embodiments of such biopsy devices, systems incorporating such biopsy devices, and methods using the same are described below. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure.

Figure 1:
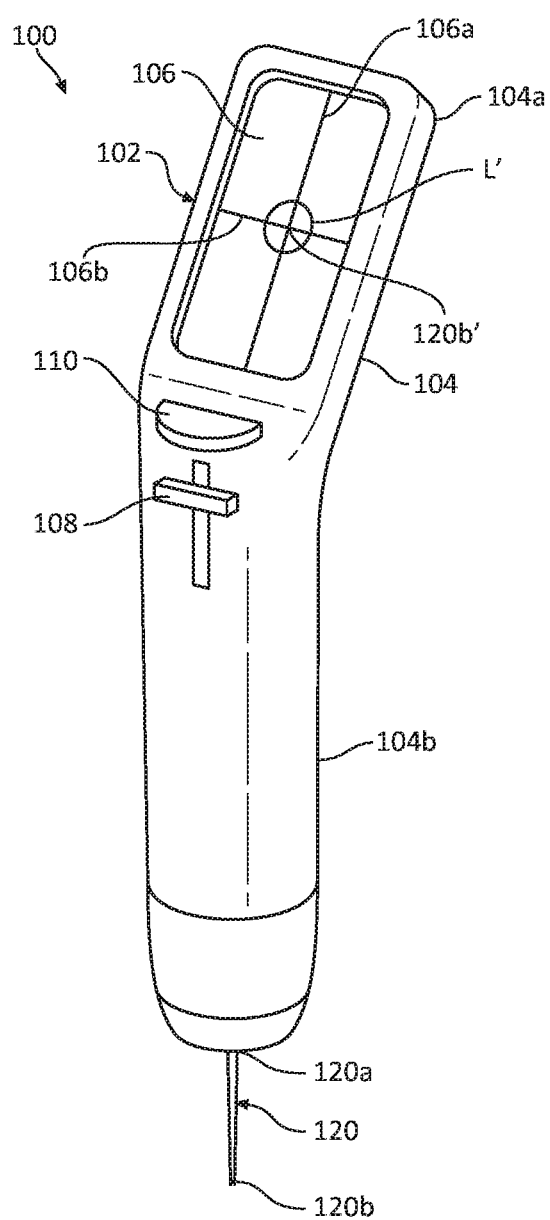
FIG. 1 is a perspective view of an ultrasonic biopsy device provided in accordance with the present disclosure configured for navigation to a target location and for obtaining a tissue sample.

With reference to FIGS. 1, 2A, and 2B, a biopsy device 100 is provided in accordance with the present disclosure for obtaining a tissue sample from a target tissue, for example, a lesion. The biopsy device 100 generally includes a handle assembly 102 and a needle 120 disposed within the handle assembly 102. The handle assembly 102 includes a handle body 104 in the form of a hand-held ultrasonic probe 104, and a display 106. The hand-held ultrasonic probe 104 is configured to perform ultrasonic imaging at a distal portion 104b thereof. Ultrasonic probe 104 has a proximal portion 104a on which the display or screen 106 is disposed. The ultrasonic probe 104 communicates with the display via a central processing unit (not shown) disposed within the probe 104 to display an image corresponding to the signals received from the probe 104.

The handle assembly 102 may house a memory (e.g., an EEPROM—not shown) for storing a variety of information regarding the biopsy device 100. In addition, the memory may store operating parameters of the biopsy device 100, e.g., power, time, RPM limits, and information regarding the usage of the biopsy device 100. Usage monitoring may enable limiting the re-use of the biopsy device 100 beyond a certain number of activations, amount of activation time, or may limit the biopsy device 100 to a single use. Such usage limitations may optionally be reset via reprocessing as is commonly understood in the art.

With continued reference to FIG. 1, the handle assembly 102 may include an adjustment mechanism 108 movably coupled to the probe 104b. In embodiments, the adjustment mechanism 108 may be configured as a slider. The adjustment mechanism 108 is in communication with the central processing unit or microprocessor (not shown) of the biopsy device 100 and is configured to adjust and set a needle depth of the needle 120, as will be described in detail below. The handle assembly 102 may include an actuator or needle firing button 110 coupled to the probe 104 and configured to fire the needle 120 into target tissue.

The needle 120 of biopsy device 100 has a proximal end portion 120a and a distal end portion 120b configured to penetrate tissue. The proximal end portion 120a of the needle 120 is operably coupled to the actuator 110 of the handle assembly 102 such that actuation of the actuator 110 distally moves the needle 120 relative to the distal end portion 104b of the probe 104 along a longitudinal axis defined by the needle 120. The needle 120 may be moved distally relative to the handle assembly 102 via a spring (not shown) that is preloaded and released upon actuation of the actuator 110. In some embodiments, any suitable mechanism for firing the needle 120 may be implemented, for example, an electromechanical drive, pressurized pneumatics, a manual drive screw, or the like. Alternately, the biopsy device 100 may be configured to connect to a remote drive and/or power source (not shown) to drive actuation of the needle 120.

The distal end portion 120b of the needle 120 is hollow such that insertion of the needle 120 into tissue captures tissue in a hollow interior defined in the needle 120. In some embodiments, the needle 120 may be configured as a cannula having a sharpened distal end. The distal end portion 120b of the needle 120 is disposed within the handle assembly 102 when the needle 120 is in the un-actuated condition, and extends distally from the handle assembly 102 when in the deployed or actuated condition. As the needle 120 moves from the un-actuated condition to the deployed condition, the needle 120 passes through an ultrasound sensor or transducer (not explicitly shown) of the probe 104 in alignment with the direction of the ultrasonic waves.

The probe 104 is configured to send ultrasonic waves toward the distal end portion 120b of the needle 120, whereby the distal end portion 120b reflects sound waves back to the probe 104, which, in turn, sends the reflected sound waves to the central processing unit of the biopsy device 100. The central processing unit generates an image of the distal end portion 120b of the needle 120 on the display 106.

With reference to FIGS. 2A and 2B, sterility of the ultrasonic probe 104 may be maintained by use of a custom cap or sterile cover 130 that is removably coupled to the distal end portion 104b of the probe 104. The sterile cover 130 serves as a barrier between the ultrasonic probe 104 and a patient's skin. Ultrasonic gel may be dispensed inside the cover 130 or may be pre-packaged with a layer of gel and a rip tab. The cover 130 defines a central opening 132 that has the needle 120 extending therethrough when the cover 130 is attached to the distal end portion 104b of the probe 104. The cover 130 permits ultrasound propagation therethrough while preventing the probe 104 from directly contacting a patient. The cover 130 may include a window 134 formed of ultrasound-opaque material.

The adjustment mechanism 108 and the actuator 110 are in communication with the central processing unit (not shown) of the handle assembly 102. As mentioned above, the adjustment mechanism 108 sets the depth that needle 120 can penetrate target tissue. Specifically, the adjustment mechanism 108 sets the amount that the needle 120 moves distally relative to the handle assembly 102 upon actuating the needle firing button 110. As such, upon actuation of the needle firing button 110, the needle 120 moves distally relative to the handle assembly 102 a selected longitudinal distance corresponding to the needle depth set by the adjustment mechanism 108.

Figure 3:
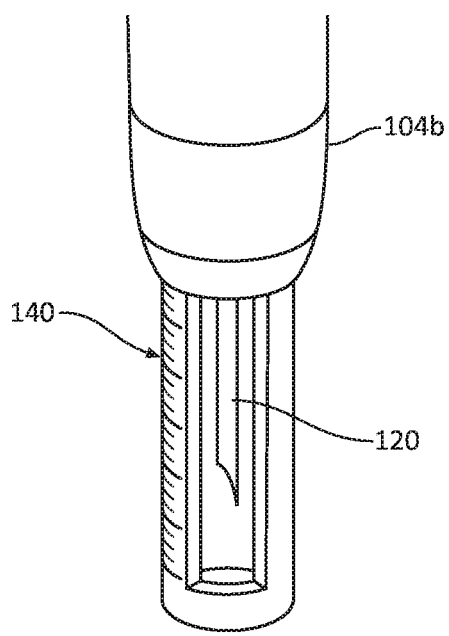
FIG. 3 is a partial perspective view of a needle depth stop attached to a needle assembly of the biopsy device of FIG. 1.

In one embodiment, as shown in FIG. 3, the biopsy device 100 may include a needle depth stop 140 extending distally from the ultrasonic probe 104. The depth stop 140 may be configured as a tube that surrounds the needle 120 of the biopsy device 100 and extends distally beyond the needle tip 120*b* of the needle 120 when the needle 120 is in the retracted position. The distance the depth stop 140 extends distally relative to the needle tip 120*b* may be manually adjusted. In this way, to set the penetration depth of the needle 120, the depth stop 140 is moved axially relative to the distal end portion 104*b* of the ultrasonic probe 104.

Figure 4:
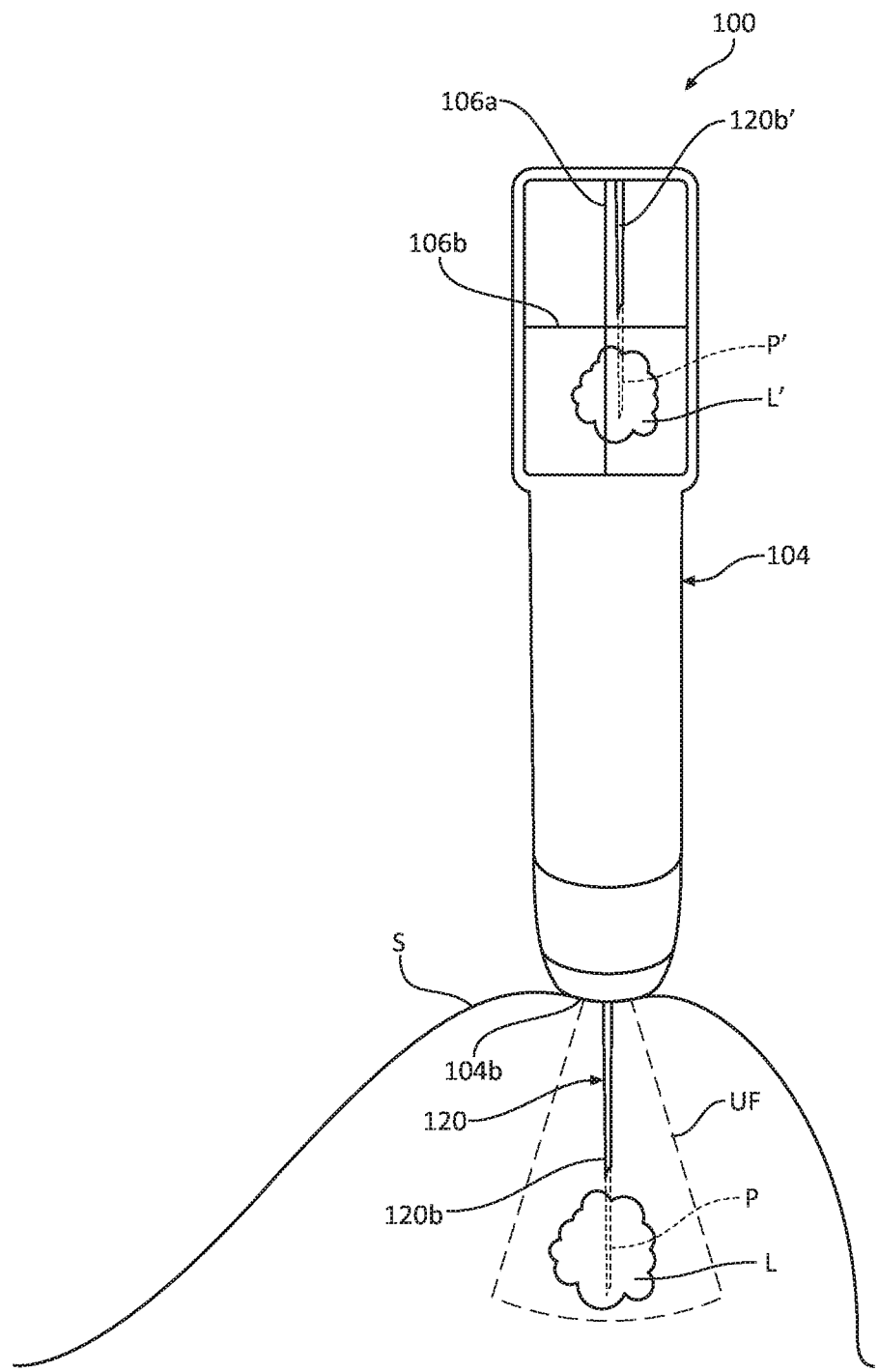
FIG. 4 is a front view of the ultrasonic biopsy device of FIG. 1 during insertion and navigation to a target tissue.

One use of the biopsy device 100 for extracting tissue samples from a lesion, e.g., a tumor, is described in detail with reference to FIGS. 1 and 4. The biopsy device 100 is positioned such that the distal end portion 104*b* of the probe 104 is placed in abutting engagement with an outer surface "S" of tissue (e.g., breast tissue), with the distal end portion 120*b* of the needle 120 in proximity to target tissue, e.g., a lesion "L." The probe 104 is activated to emit an ultrasonic field "UF" toward the lesion "L" and the distal end portion 120*b* of the needle 120. The probe 104 then receives the reflected sound waves and the central processing unit (not shown) of the probe 104 generates an image of the distal end portion 120*b*' of the needle 120 relative to the lesion "L'" on the display 106. In addition, the central processing unit of the biopsy device 100 may animate a projected needle pathway "P'" on the display 106 such that a clinician can accurately predict the pathway "P'" the needle 120 will travel at any given moment if actuated. The biopsy device 100 is moved to a position in which the projected needle pathway "P'" animated on the display 106 is aligned with the image of the lesion "L.'" At this time, or at any suitable time, the adjustment mechanism 108 (FIG. 1) may be moved to set the needle depth of the needle 120. Alternatively, if the depth stop 140 (FIG. 3) is provided, the depth stop 140 may be moved to set the needle depth of the needle 120. The cross-hairs 106*a* and 106*b* on the display 106 provide guidance relating to the depth of the needle 120 when deployed.

Figure 11:
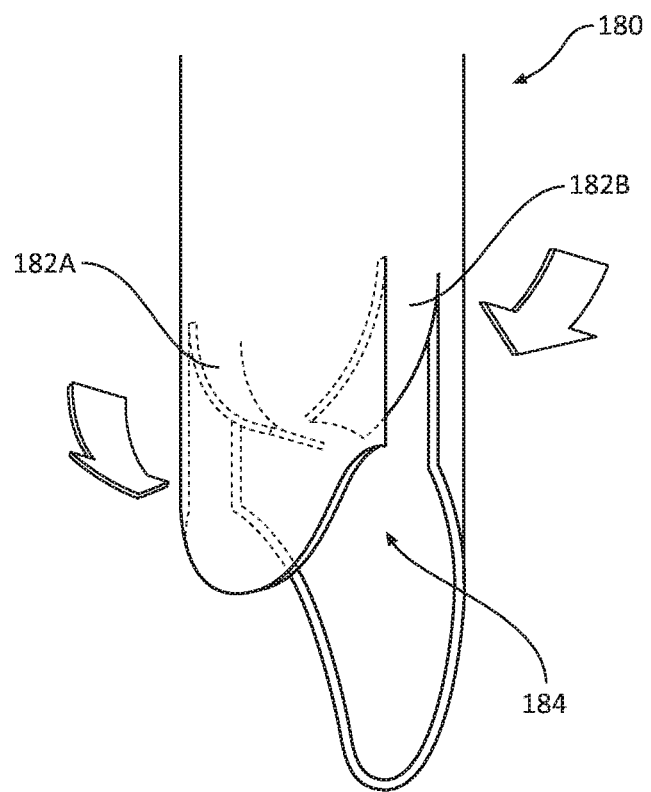
FIG. 11 is a partial perspective view of another embodiment of a needle for use with the ultrasonic biopsy device of FIG. 1.

Upon aligning, on the display 106, the projected needle pathway "P'" with the displayed image of the lesion "L,'" on the display 106, the needle actuator 110 may be actuated to move the needle 120 along the projected needle pathway "P'" in situ a longitudinal distance corresponding to the needle depth set by the adjustment mechanism 108. In some embodiments, the biopsy device 100 may be moved manually in the distal direction to penetrate the lesion "L" with the needle 120. As the needle 120 penetrates the lesion "L," a first tissue sample of the lesion "L" enters the distal end portion 120*b* of the needle 120. In some embodiments, the needle 120 is a center coring needle. In other embodiments, as shown in FIG. 11, the needle 120 may be a side-biting needle.

Figure 5A:
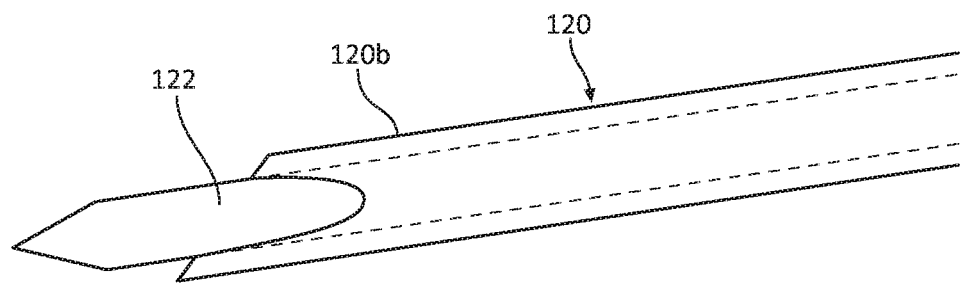
FIG. 5A is a side view of a needle of the biopsy device of FIG. 1.
Figure 5B:
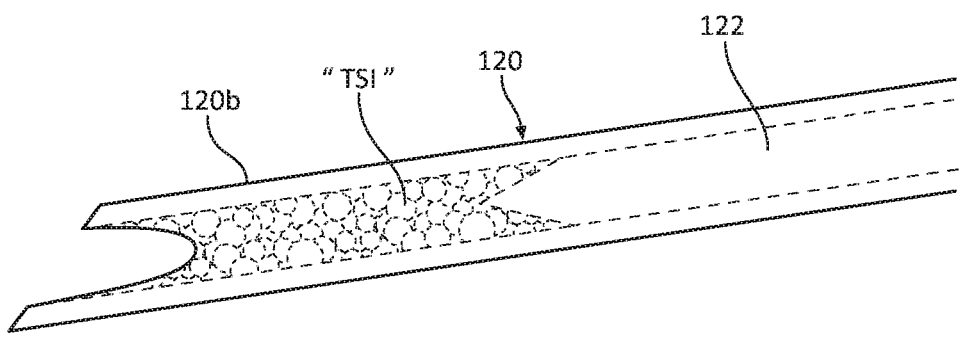
FIG. 5B is a side view of the needle of FIG. 5A having a sample of tissue disposed therein.
Figure 7A:
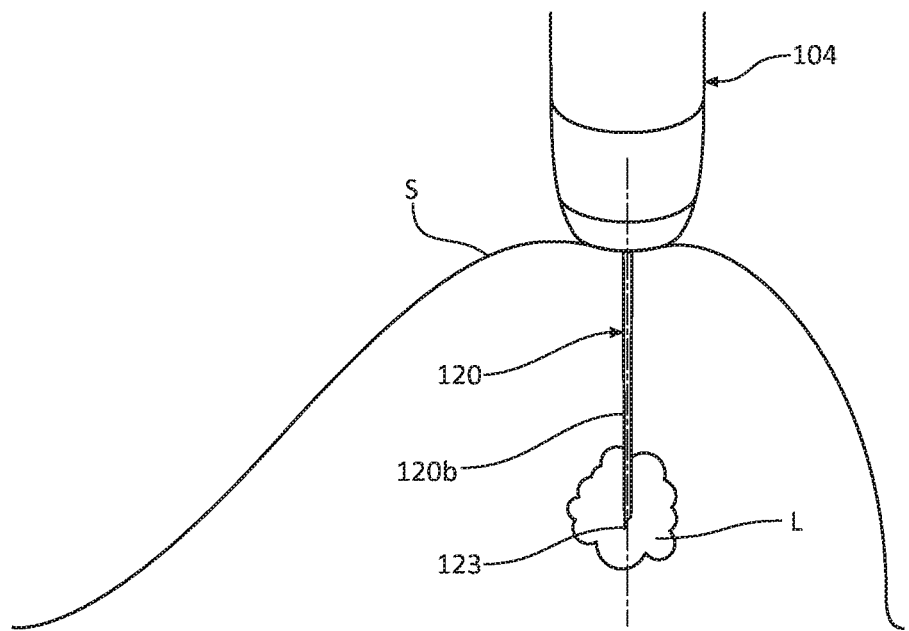
FIGS. 7A-7D illustrate a method of extracting two tissue samples using the ultrasonic biopsy device of FIG. 1.
Figure 7B:
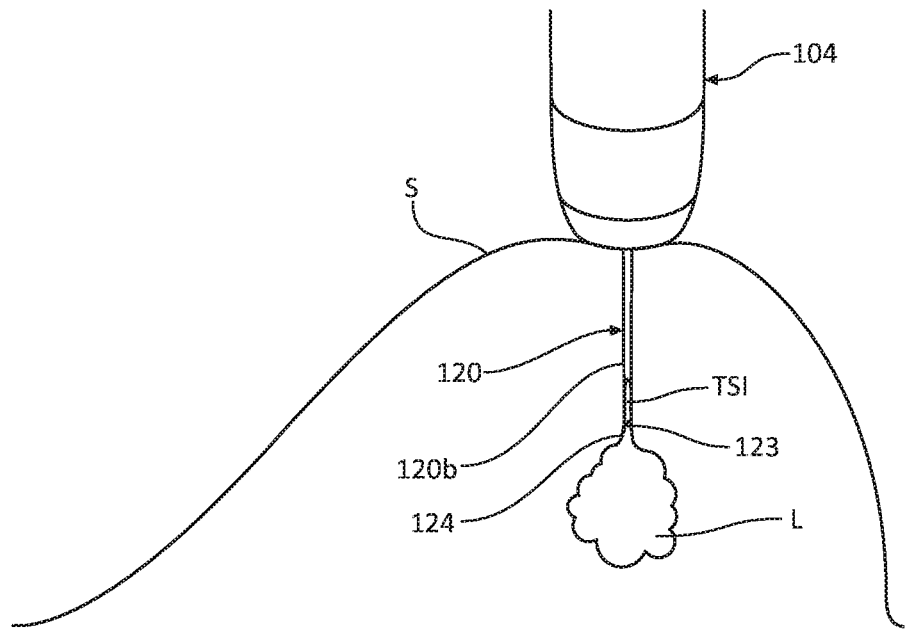
Figure 7C:
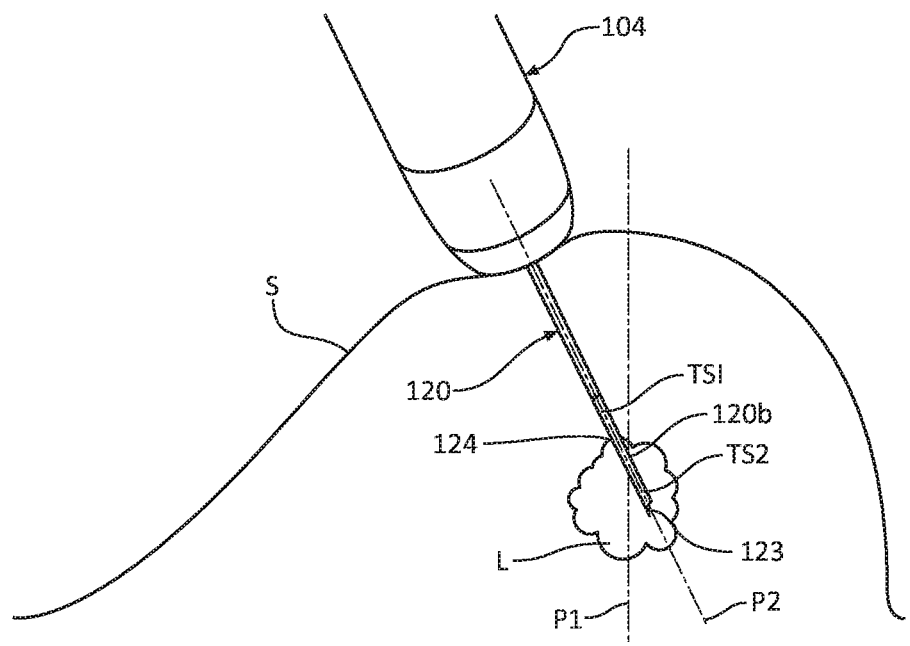
Figure 7D:
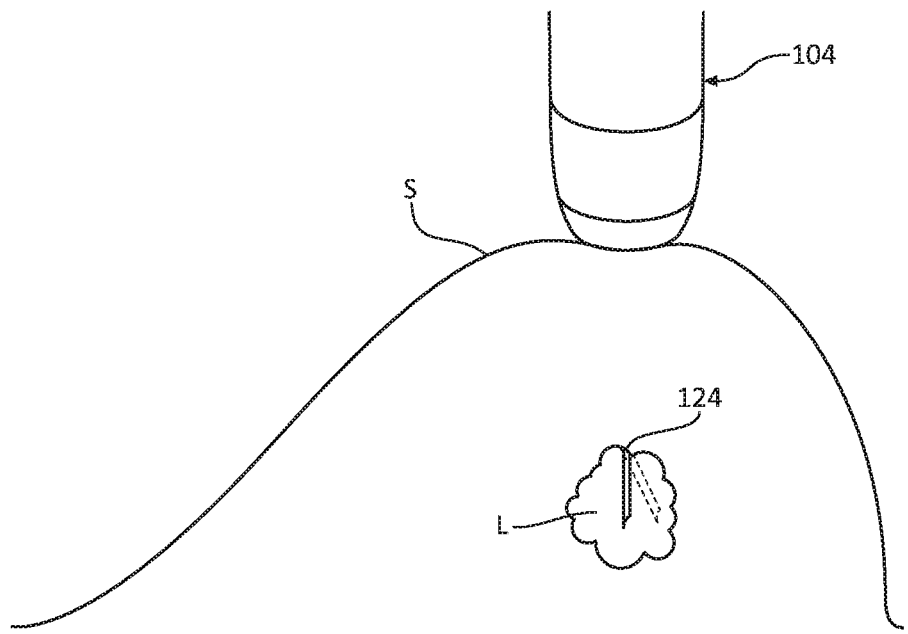

With reference to FIGS. 5A and 5B, in some embodiments, prior to driving the distal end portion 120*b* of the needle 120 into the lesion "L," a stylet 122 may be driven through the needle 120 and into the lesion "L" to act as an introducer and to control the starting point of the tissue sample. After inserting the stylet 122, the stylet 122 may be retracted back into the needle 120, and the needle 120 may then be driven distally into the lesion "L." Alternately, instead of manually retracting the stylet 122 back into the needle 120, distal penetration of the needle 120 into the lesion "L" may drive the stylet 122 back into the needle 120 allowing the first tissue sample "TS1" to enter the distal end portion 120*b* of the needle 120.

With reference to FIGS. 6A-6D, various methods may be employed to more effectively extract the first tissue sample "TS1" from the lesion "L" and into the needle 120. For example, with reference to FIG. 6A, the needle 120 may be vibrated inside of the lesion "L." The needle 120 may be vibrated using the ultrasound probe 104, a vibration motor, transducer, or any suitable mechanism capable of causing the needle 120 to vibrate. With reference to FIG. 6B, the needle 120 may be swung or pivoted about an axis that extends perpendicularly through the needle 120. With reference to FIG. 6C, the needle 120 may be configured as an electrosurgical needle capable of emitting high frequency radiation to assist in extraction of the first tissue sample "TS1." With reference to FIG. 6D, the distal end portion 120*b* of the needle 120 may be first inserted into the lesion "L," extracted from the lesion "L," pivoted relative to the lesion "L" to a different angle, and then re-inserted into the lesion "L" at the different angle. With reference to FIG. 6E, the needle 120 may be rotated about its longitudinal axis to assist in tissue extraction.

In some embodiments, after capturing the tissue sample "TS1" in the needle 120, a vacuum may be established proximally of the needle 120 by a one-way valve (not shown) or by drawing a negative vacuum with a syringe or pump. The tissue sample "TS1" may be collected within the needle 120 or in a tissue chamber (not shown) of the needle 120. Suction may be applied in a controlled manner so as to maintain the tissue sample "TS1" intact. In some embodiments, a vacuum or suction source may be used to trap the tissue sample "TS1" within the needle 120. In some embodiments, the biopsy system 100 may include a tissue containment chamber that collects tissue samples for testing. In one embodiment, a pressurized fluid may be used to drive the tissue sample "TS1" from the needle into the tissue chamber.

With reference to FIGS. 7A-7D, after inserting the distal end portion 120*b* of the needle 120 into the lesion "L," the distal end portion 120*b* of the needle 120 may be withdrawn from the lesion "L" carrying the first tissue sample "TS1" therein. Proximal withdrawal of the distal portion 120*b* of the needle 120 from the lesion "L" is continued until a distal-most point 123 of the needle 120 reaches an entry hole 124 defined in the outer surface of the lesion "L." While maintaining the distal-most point 123 of the needle 120 at the entry hole 124, the needle 120 is then angled relative to the lesion "L" such that the needle 120 assumes a second projected needle pathway "P2," angled relative to the first needle pathway "P1." The needle 120 is then re-inserted into the access hole 124 along the second pathway "P2," thereby capturing a second tissue sample "TS2" of the lesion "L" in the needle 120. In some embodiments, rather than re-inserting needle 120 into access hole 124 a second time, the needle 120 may be inserted through a different hole (not shown) of lesion "L" to capture the second tissue sample "TS2." The needle 120 is then retracted into the probe 104 and out of the tissue.

The tissue samples "TS1," "TS2" may be discharged out of the distal-most end 124 of the needle 120, or be removed from a syringe-portion of the needle 120. In some embodiments, the tissue samples "TS1," "TS2" may be expelled from the needle 120 using a tissue sample removal system (not shown) coupled to the biopsy device 100 which discharges a fluid (e.g., air or liquid) distally through needle 120. In some embodiments, the tissue sample removal system may be integrally formed with the biopsy device 100.

In embodiments, the biopsy device 100 may include a mechanism configured to deploy a marker or tracking device into the lesion "L." For example, the needle 120 may include a spring configured to deploy the marker from the distal-most end 124 of the needle 120 or a side opening in the needle 120. After deployment of the marker, the needle 120 may be automatically retracted into the biopsy device 100. In embodiments, upon the needle 120 terminating its deployment, the biopsy device may automatically capture an image of the tissue sample disposed in the needle 120 or at the instant the needle 120 penetrates the tissue sample.

Figure 8A:
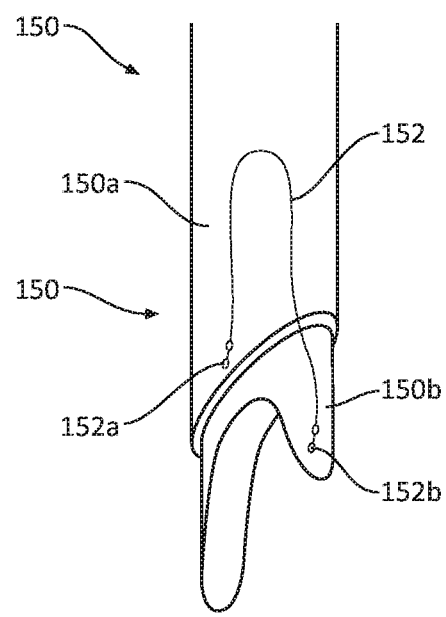
FIG. 8A is a partial perspective view of another embodiment of a needle assembly for use with the ultrasonic biopsy device of FIG. 1.
Figure 8B:
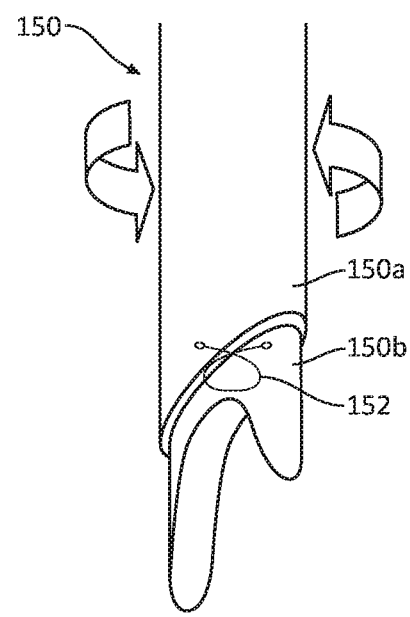
FIG. 8B is a partial perspective view of the needle assembly of FIG. 8A after rotation thereof.

In one embodiment, as shown in FIGS. 8A and 8B, the needle 120 of the biopsy device 100 may be replaced with a side-biting needle 150, which includes an outer cannula 150a and a notched inner cannula or rod 150b disposed within the outer cannula 150a. The side-biting needle 150 may include a wire 152 having a first end 152a attached to a distal end portion of the outer cannula 150a and a second end 152b attached to a distal end portion of the inner cannula 150b. When the side-biting needle 150 is actuated, the notched inner cannula 150b is deployed into the lesion "L" followed by a rotating of the cannulas 150a, 150b relative to one another to sever the tissue with the wire 152. Only one of the cannulas 150a, 150b may be configured to rotate with respect to the other of the cannulas 150a, 150b. After deployment, the inner and outer cannulas 150a, 150b are retracted into the handle assembly 102.

Figure 9:
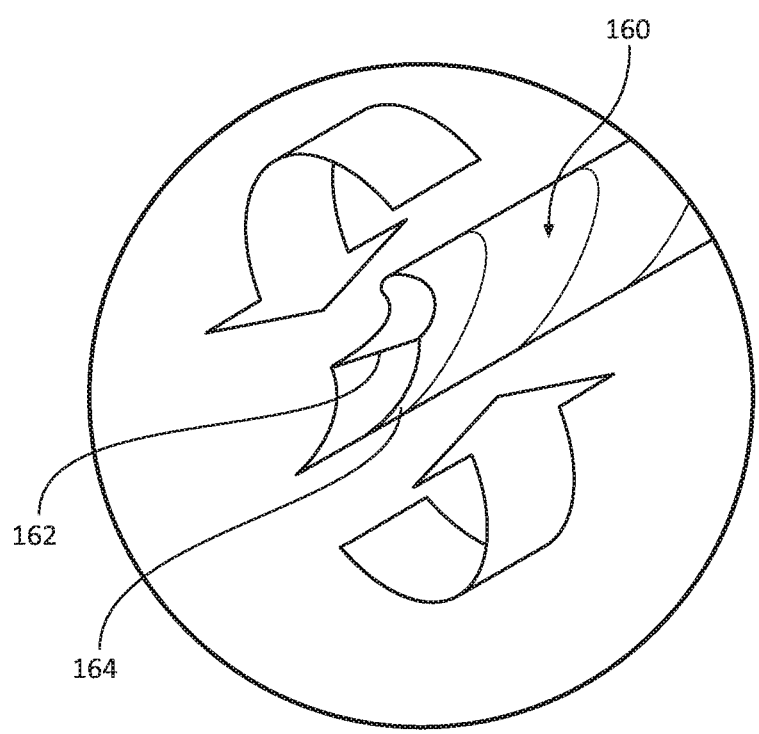
FIG. 9 is a partial perspective view of another embodiment of a needle for use with the ultrasonic biopsy device of FIG. 1.

In another embodiment, as shown in FIG. 9, the needle 120 of the biopsy device 100 may be replaced with another embodiment of a needle 160 that includes a metal wire 162 that extends across a tip 164 of the needle 160. In embodiments, the wire 162 may be any suitable material capable of severing tissue. In use, after the needle 160 captures a tissue specimen therein, the needle 160 is rotated about its longitudinal axis. During rotation of the needle 160, the wire 162 severs the tissue specimen at its base allowing for its removal from the tissue site.

Figures 10A, 10B:
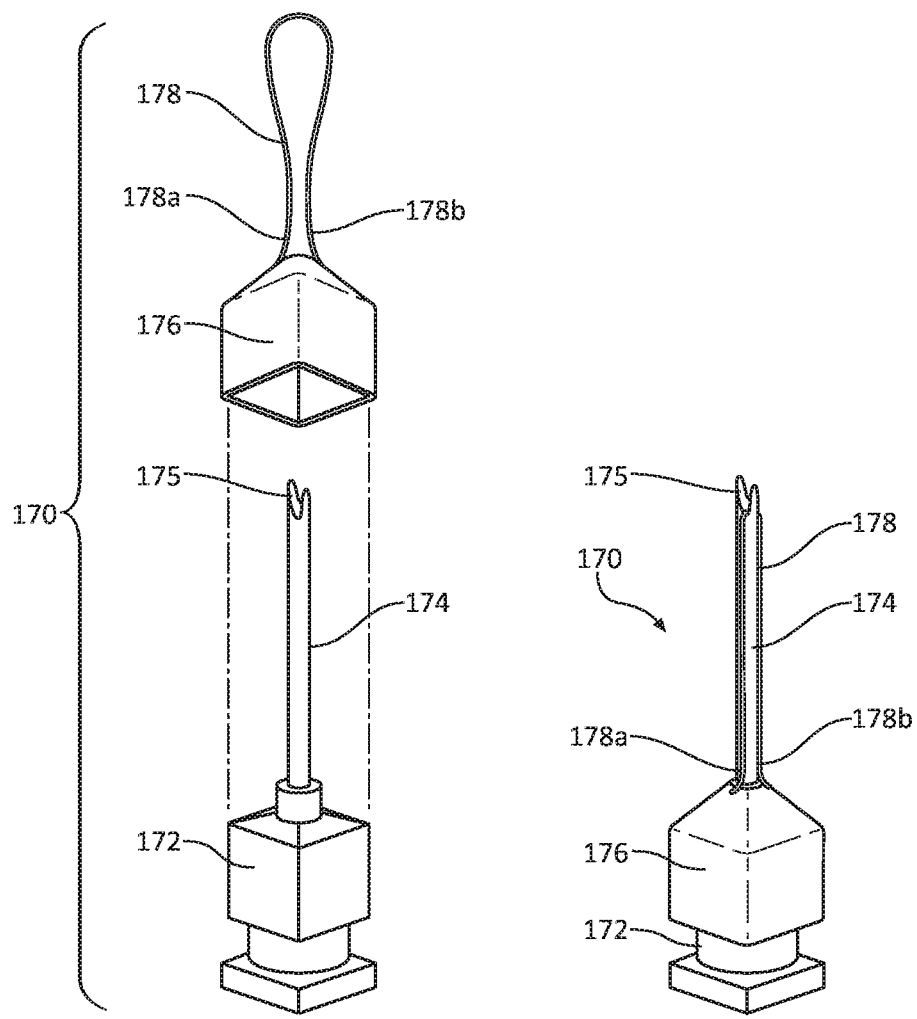
FIG. 10A perspective view, with parts separated, of another embodiment of a needle assembly for use with the ultrasonic biopsy device of FIG. 1.
FIG. 10B is a perspective view of the needle assembly of FIG. 10A in an assembled state.

In yet another embodiment, as shown in FIGS. 10A and 10B, the needle 120 of the biopsy device 100 may be replaced with a needle assembly 170, which includes a hub or body 172 and a needle 174 extending distally therefrom. The needle assembly 170 may further include a hub cover 176 configured to fit over the hub 172 of the needle assembly 170, and a wire 178 having opposing ends 178a, 178b attached to opposing sides of the hub cover 176. Upon positioning the hub cover 176 over the hub 172, the wire 178 extends taught across a needle tip 175 of the needle 174. In use, after the needle 174 captures a tissue specimen therein, the needle assembly 170 is rotated about its longitudinal axis. During rotation of the needle assembly 170, the wire 178 severs the tissue specimen at its base allowing for its removal from the tissue site.

In some embodiments, the needle of the biopsy device 120 may include a barb or hook that extends into the internal passageway of the needle. The barb may be configured to allow for the passage of tissue into the internal passageway, but inhibit the tissue from moving distally out of the needle.

With reference to FIG. 11, another embodiment of a needle 180 to be used with the biopsy device 100 is illustrated. The needle 180 includes a pair of flaps 182a, 182b formed with a distal end portion of the needle 180. The flaps 182a, 182b are configured to move from a first state in which the flaps 182a, 182b extend in line with an outer surface of the needle 180, and a second state (as shown in FIG. 11) in which the flaps 182a, 182b extend into an internal passageway 184 of the needle 180. The tabs 182a, 182b may be fabricated from a shape memory alloy, e.g., nitinol, configured to move from the first state to the second state upon receiving an electrical impulse or upon changing to a particular temperature (e.g., body temperature). In use, the needle 180 is deployed into tissue with the tabs 182a, 182b in their first state. After the needle 180 captures a tissue specimen therein, the tabs 182a, 182b are shifted toward their second state (e.g., via receiving an electrical impulse), and ends of the tabs 182a, 182b cut into the tissue specimen at its base allowing for its removal from the tissue site.

With reference to FIGS. 12A-12E, another embodiment of a needle assembly 190 for use with the biopsy device 100 is illustrated. The needle assembly 190 includes a hollow hub or body 192 and a needle 194 extending distally therefrom and in fluid communication therewith. The needle assembly 190 further includes a tube 196 attached to or formed with an outer surface of the needle 194. The tube 196 extends parallel with and alongside the length of the needle 194. The tube 196 defines a channel 198 therethrough which acts as a ventilation channel to mitigate a tissue suction effect that may occur during removal of a tissue specimen from tissue "T."

In use, upon inserting the needle 194 of the needle assembly 190 into tissue "T," the tube 196 has a rod (not shown) disposed in the channel 198 of the tube 196 to prevent tissue from entering the channel 198 of the tube 196. The needle assembly 190 is rotated about its longitudinal axis to sever a tissue specimen captured in the needle 194. As the needle assembly 190 is rotated, the tube 196 radially expands the hole "H" formed by the needle 194 upon entering the tissue "T" to form a space "S" between the needle 194 and the tissue "T." As the needle assembly 194 is extracted from the tissue "T," the rod is removed from the channel 198 of the tube 196 to allow air to travel through the channel 198 and into the hole "H" formed in the tissue "T." This has the effect of preventing a vacuum from being formed in the hole "H" of the tissue "T" during removal of the needle 194, which would otherwise cause the tissue specimen to be drawn distally out of the needle 194 during extraction.

Figures 13A, 13B:
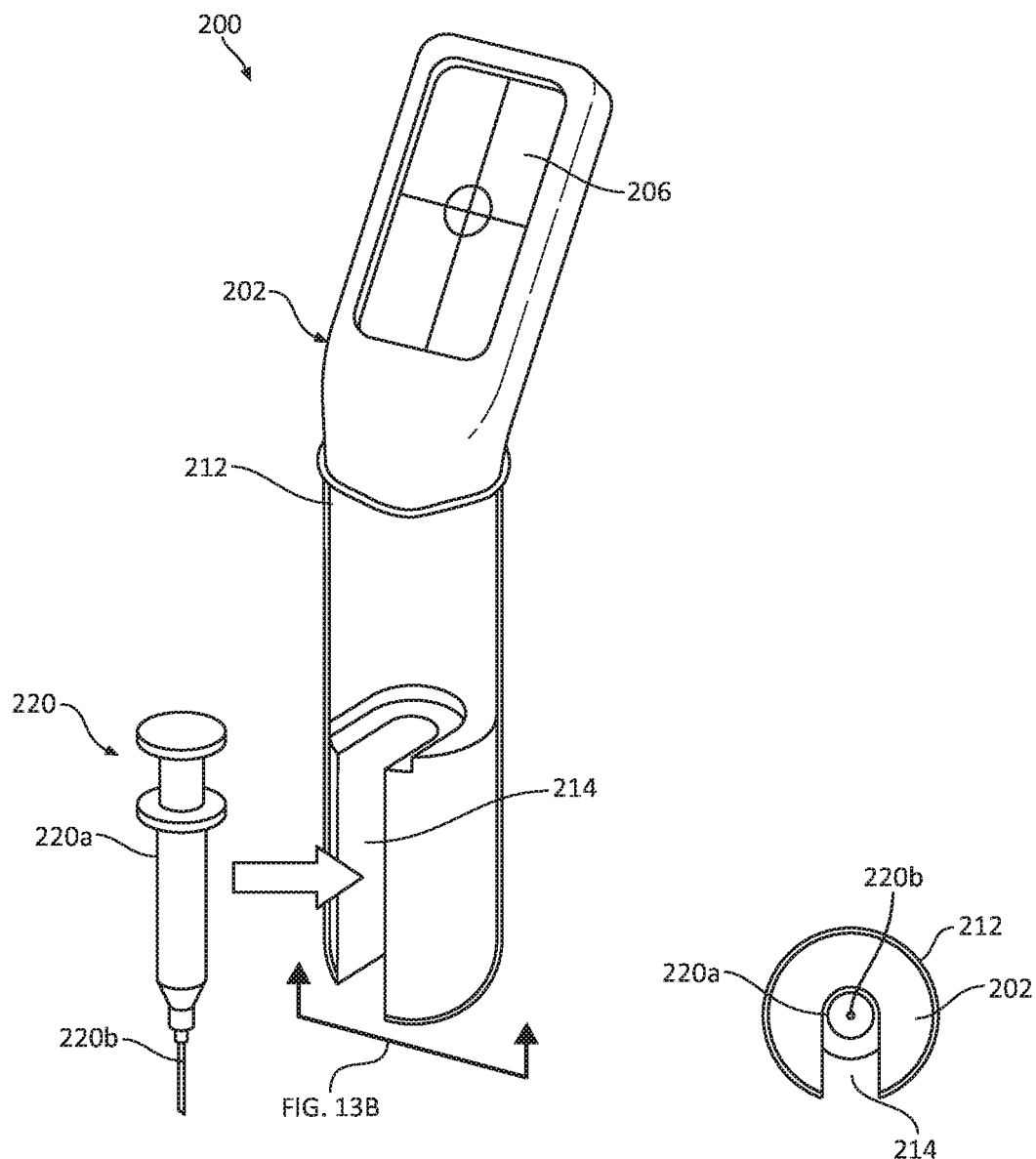
FIG. 13A is a perspective view of another embodiment of a biopsy device in accordance with the present disclosure.
FIG. 13B is a bottom view of the biopsy device of FIG. 13A.

With reference to FIGS. 13A and 13B, another embodiment of a biopsy device 200 is provided. The biopsy device 200 is substantially similar to the biopsy device 100 described above. Accordingly, the biopsy device 200 will only be described in sufficient detail to elucidate selected differences from biopsy device 100. The biopsy device 200 includes a handle assembly 202, and a needle assembly or cartridge 220 configured to be removably coupled to the handle assembly 202. The handle assembly 202 may be an ultrasonic probe having a display 206 for displaying an ultrasonic image. The handle assembly 202 includes a sheath or protective sleeve 212 configured to cover a distal portion of the handle assembly 202. The sleeve 212 permits ultrasound propagation therethrough while preventing the handle assembly 202 from directly contacting a patient. The sleeve 212 may include a window formed of ultrasound-opaque material. In some embodiments, the sleeve 212 may have pre-applied ultrasound gel disposed on a portion or portions thereof.

The handle assembly 202 has a longitudinally-extending channel 214 defined in the distal portion thereof. Needle assembly 220 includes a medical syringe 220a fitted with a needle 220b. The channel 214 is configured to receive the needle assembly 220 therein. In some embodiments, the protective sleeve 212 and/or the channel 214 may be incorporated into the biopsy device 100 of FIG. 1. The needle assembly 220 may be actuated or deployed in a similar manner as described herein (e.g., via biasing members) or in any other suitable way known in the art. During actuation, the needle assembly 220 is moved relative to the handle assembly 202 distally along a longitudinal axis defined by the biopsy device 200.

Figure 14:
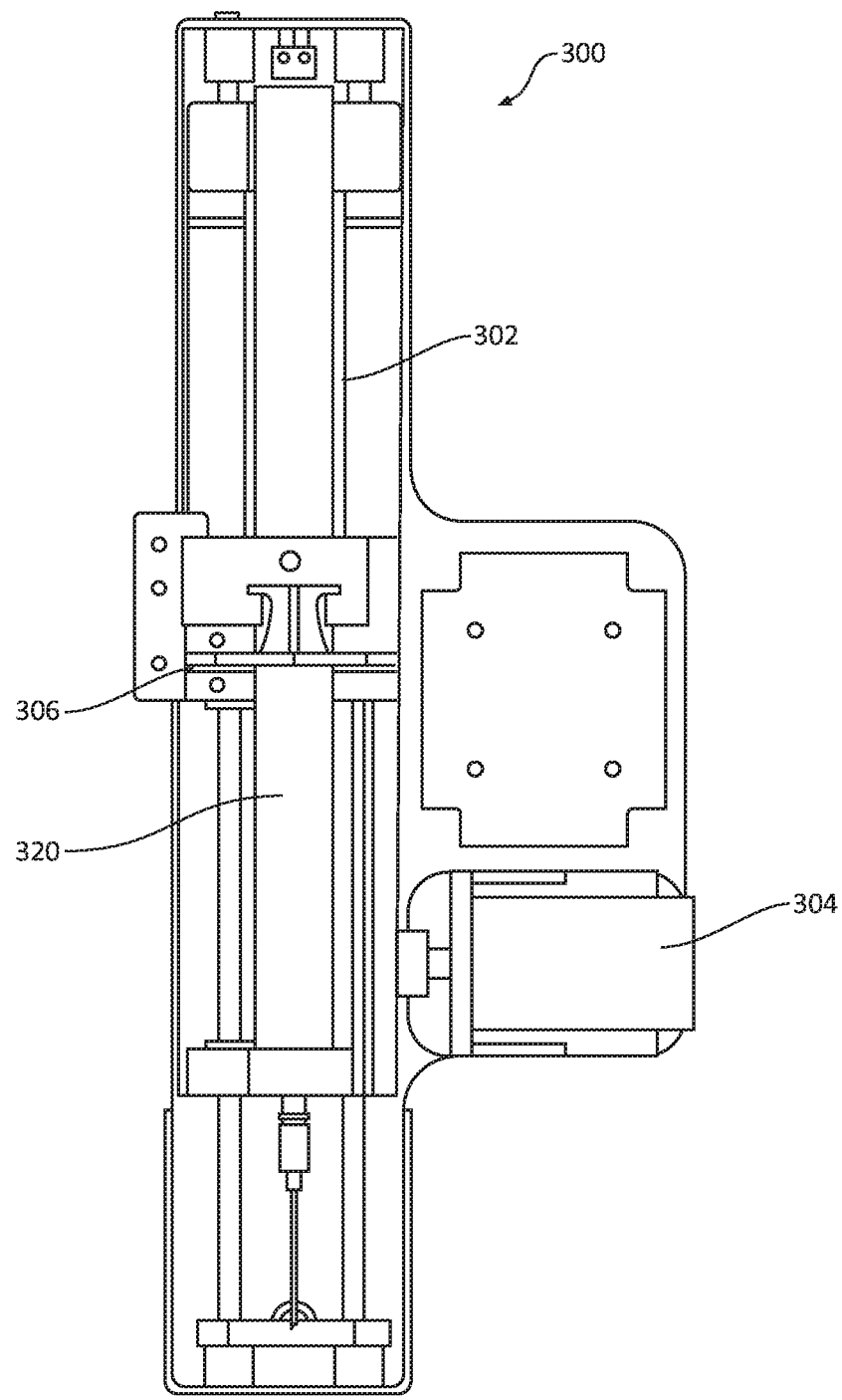
FIG. 14 is a front view of yet another embodiment of a biopsy device in accordance with the present disclosure.

With reference to FIG. 14, another embodiment of a biopsy device 300 is illustrated. The biopsy device 300 is substantially similar to the biopsy device 100 described above. Accordingly, the biopsy device 300 will only be described in sufficient detail to elucidate selected differences from biopsy device 100. The biopsy device 300 includes an actuation spring 302 and a motor 304 for driving actuation of a needle 320 of the biopsy device 300. The motor 304 raises a platform 306 on which the needle assembly 320 is supported to compress or load the actuation spring 302. Upon setting the motor 304 in neutral, the load of the actuation spring 302 drives the needle assembly 320 in a distal direction.

Figure 15A:
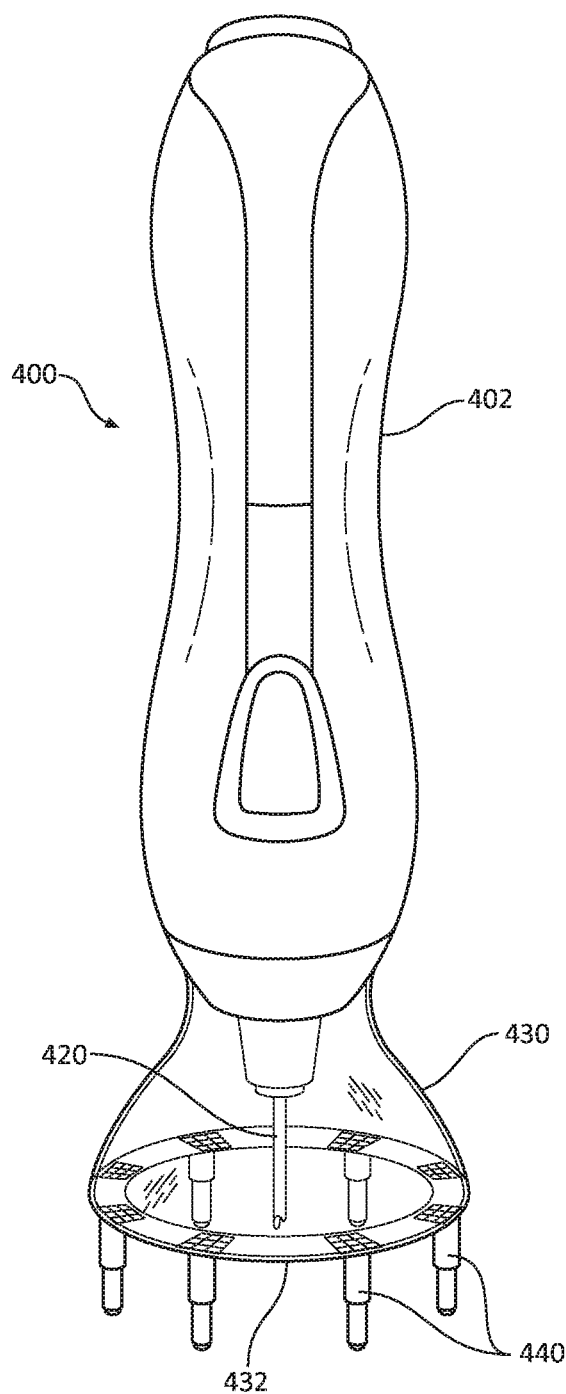
FIG. 15A is a perspective view of still yet another embodiment of a biopsy device in accordance with the present disclosure including a plurality of force sensors.
Figure 15B:
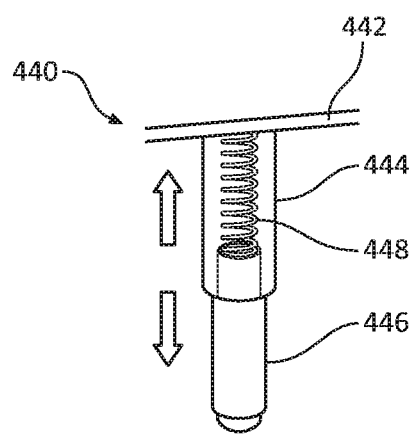
FIG. 15B is an enlarged perspective view of one of the force sensors of the biopsy device of FIG. 15A.

With reference to FIGS. 15A and 15B, another embodiment of a biopsy device 400 is illustrated. The biopsy device 400 is substantially similar to the biopsy device 100 described above. Accordingly, the biopsy device 400 will only be described in sufficient detail to elucidate selected differences from biopsy device 100. The biopsy device 400 includes a handle body 402, a needle assembly 420 connected to the handle assembly 402, and a collar or annular member 430 extending distally from the handle body 402. The collar 430 encapsulates the needle assembly 420 and extends distally beyond a distal-most end of the needle assembly 420 when the needle assembly 420 is in an unactuated position.

The biopsy device 400 includes a plurality of force sensors 440 disposed in an annular array on a distally-oriented surface 432 of the collar 430. In some embodiments, the force sensors 440 and/or the collar 430 may be incorporated into the biopsy device 100. Each sensor 440 has a sensor plate 442 fixedly coupled to the distally-oriented surface 432 of the collar 430, a proximal body 444 fixed to the sensor plate 442, and a distal body 446 that is slidably coupled to the proximal body 444. Each sensor 440 has a biasing member, such as, for example, a coil spring 448, disposed between the proximal and distal bodies 444, 446 of each of the sensors 440, to resiliently bias the distal body 446 away from the proximal body 444.

The force sensors 440 are in communication with a central processing unit or processor (not shown) of the handle assembly 402. The force sensors 440 relay the forces sensed by each force sensor 440 to the processor, which sends the signals to a user interface, for example, a display (not shown). In this way, the force sensors 440 may allow for the determination of an amount of resistance of the tissue against the needle assembly 420, which can be used to confirm that a targeted lesion has been correctly targeted, and that the needle assembly 420 has passed through the lesion and has not struck critical structures such as a chest wall.

Figure 16:
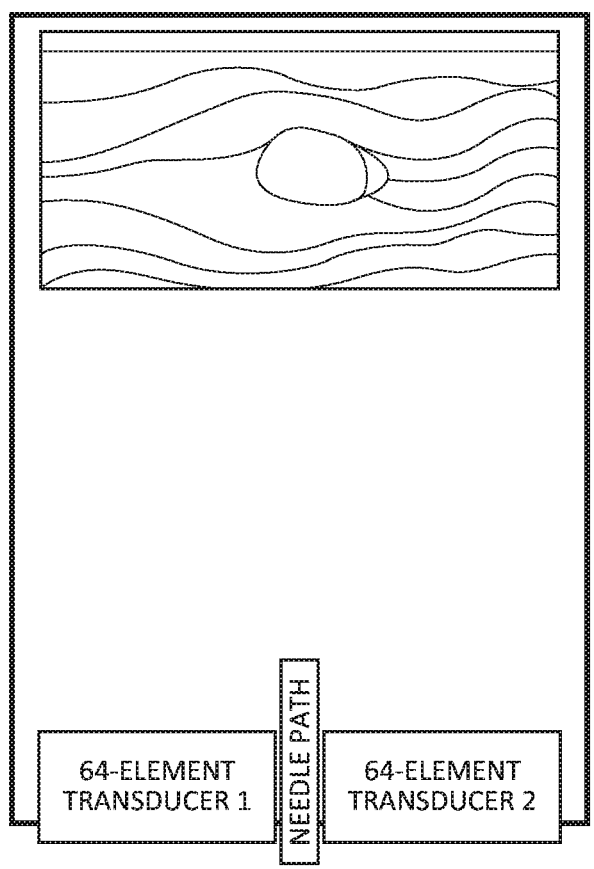
FIG. 16 is a schematic view of the ultrasonic biopsy device illustrating a pathway for a needle.

With reference to FIGS. 16-19, two 64-element transducer arrays are oriented to allow a needle pathway between them. The signal may be processed in one of at least two ways. With reference to FIG. 16, one way to process the signal is two 8-channel handheld ultrasound modules that generate ultrasound pulses and sample reflected signals. Each module performs synthetic aperture beamforming independently and the beamformed data is then merged in a processor into B-mode images. The scan sequence of this mode is illustrated in FIG. 16. The processor then sends the merged data on a USB connection to a computer with software that reads the beamformed data from the USB and displays a B-mode image on the screen.

Figure 17:
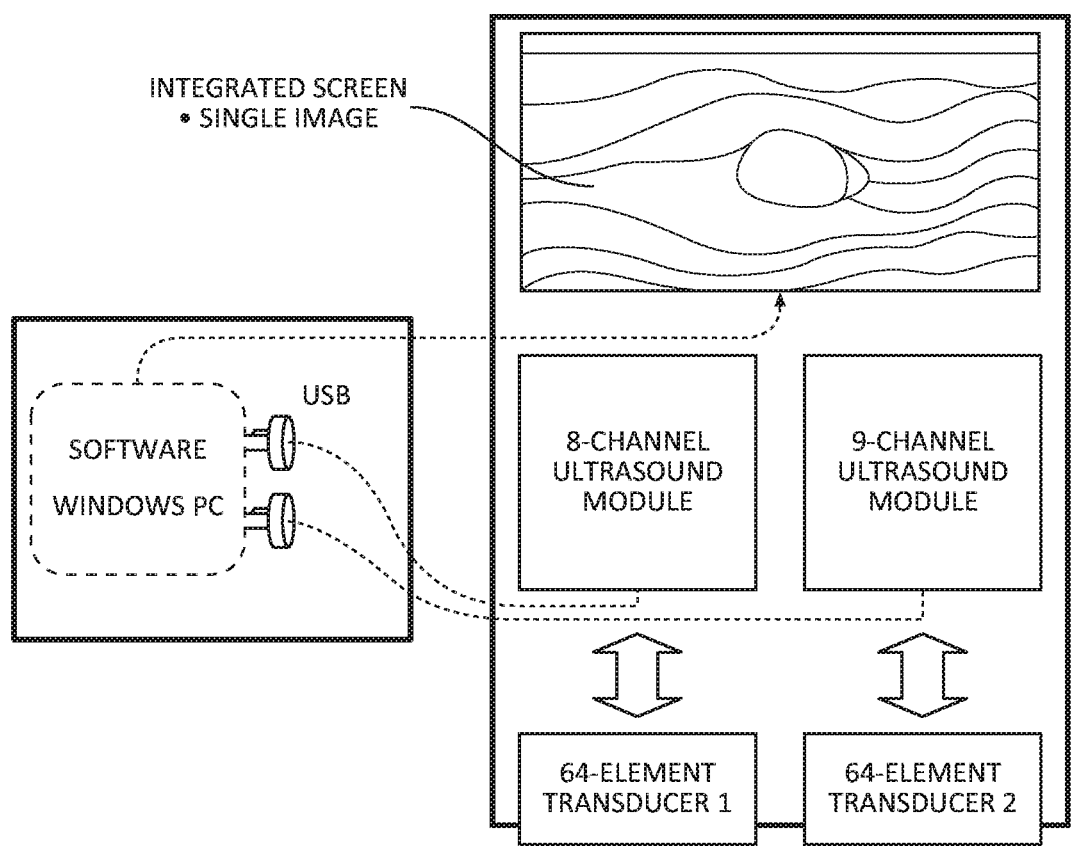
FIG. 17 is a schematic view of the ultrasonic biopsy device illustrating 8 and 9 channel ultrasound modules.
Figure 18:
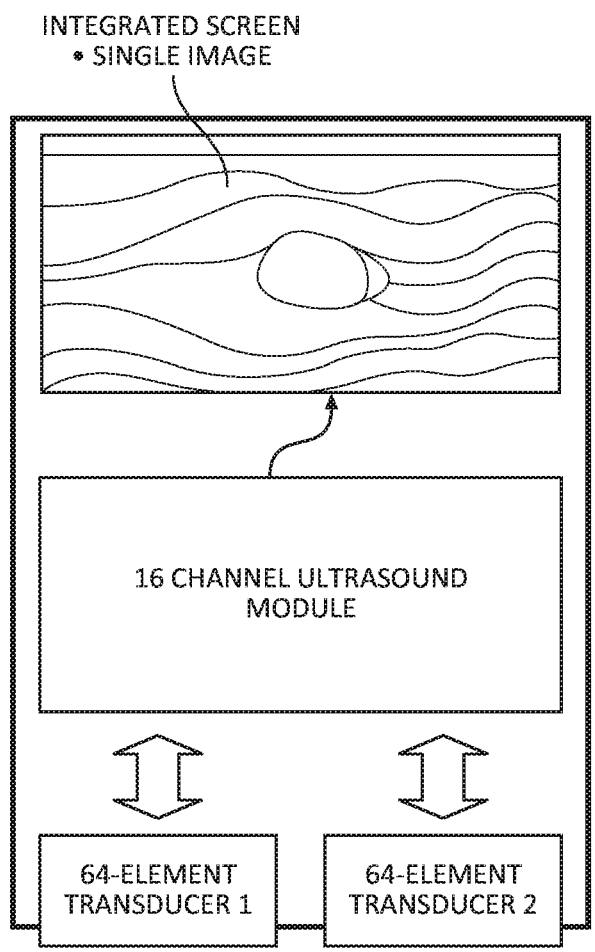
FIG. 18 is a schematic view of the ultrasonic biopsy device illustrating one ultrasound module.

With reference to FIG. 17, another way of processing the signal is a single 16-channel handheld ultrasound module used with synthetic aperture beamforming. The transmitter fires spherical waves individually or with every two elements, instead of firing focused beams with a wider transducer aperture. One advantage of employing the synthetic aperture method is it offers flexibility in configuring the transducers. In this case, by using a single beamformer, it enables placing two or more separate transducer arrays at different positions and possibly different orientations without creating a mismatch at the border of two half images. The scan sequence is shown in FIG. 18. The ultrasound image is constructed either after each cycle of the aperture coverage, or after each firing.

Figure 20C:
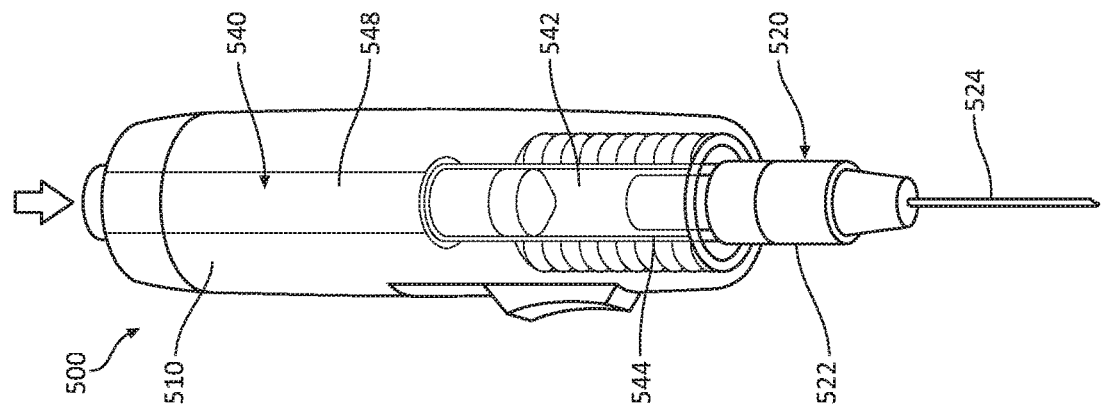
FIGS. 20A-20C illustrate a method of using another embodiment of a biopsy device.
Figure 20B:
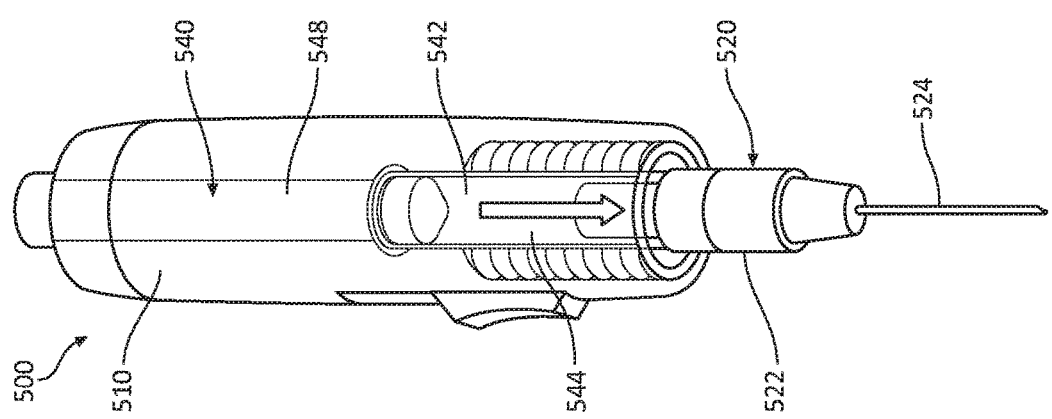
Figure 20A:
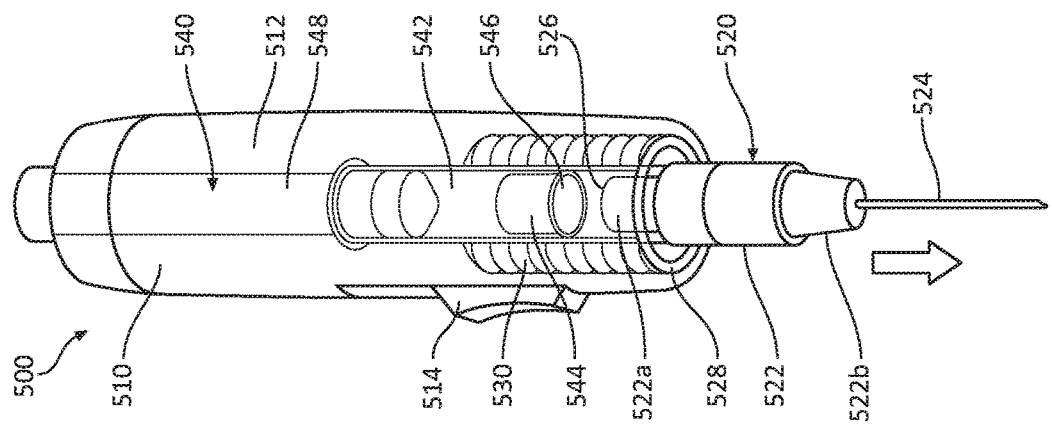

With reference to FIGS. 20A-20C, another embodiment of a biopsy device 500 is illustrated. The biopsy device 500 includes a handle assembly 510 and a needle assembly or cartridge 520 extending distally from the handle assembly 510. The handle assembly 510 incorporates an ultrasonic transducer (not explicitly shown) such that the handle assembly 510 acts as an ultrasonic probe. In embodiments, the handle assembly 510 of the biopsy device 500 may be devoid of an ultrasonic transducer.

The needle assembly 520 includes a body or hub 522 and a needle 524 extending distally from the body 522. The body 522 of the needle assembly 520 has a proximal end 522*a* disposed within an internal chamber 512 defined in the handle assembly 510, and a distal end 522*b* disposed distally of the handle assembly 510. The proximal end 522*a* of the body 522 defines an opening 526 in fluid communication with the internal chamber 512 of the handle assembly 510. The body 522 of the needle assembly 520 includes a flange 528 extending radially outward of the proximal end 522*a* thereof. A biasing member 530 (e.g., a spring) is disposed between the flange 528 of the body 522 and an internal structure of the handle assembly 510 to resiliently bias the needle assembly 520 in a distal direction. As such, upon an actuation of an actuator 514 of the handle assembly 510, the needle assembly 520 is released, thereby allowing the biasing member 530 to move the needle assembly 520 in a distal direction from a retracted position to a deployed position.

The biopsy device 500 also includes a syringe 540 axially aligned with the needle assembly 520 and disposed within the handle assembly 510. A tube 542 of the syringe 540 has a distal end 544 defining an opening 546 dimensioned for receipt of the proximal end 522*a* of the body 522 of the needle assembly 520. The syringe tube 542 of the biopsy device 500 contains a fluid (e.g., water) therein. In embodiments, the syringe tube 542 may include a gas. A plunger 548 of the syringe 540 is movably disposed within the syringe tube 542. Upon coupling the distal end 544 of the syringe tube 542 with the proximal end 522*a* of the body 522 of the needle assembly 520, the syringe tube 542 and the body 522 of the needle assembly 520 form a fluid-tight seal with one another. The distal end 544 of the syringe tube 542 may include a valve configured to remain closed until the body 522 of the needle assembly 520 is received therein.

In use, the needle assembly 520 is deployed to capture a tissue specimen in the needle 524 of the needle assembly 520. With the tissue specimen captured in the needle 524, the plunger 548 is moved distally to advance the syringe tube 542 into engagement with the body 522 of the needle assembly 520. As mentioned above, coupling the syringe tube 542 with the body 522 of the needle assembly 520 forms a fluid-tight seal between the opening 526 in the proximal end 522*a* of the body 522 of the needle assembly 520 and the opening 546 defined in the distal end 544 of the syringe tube 542. As the biopsy device 500 is withdrawn from the tissue site, the liquid disposed in the syringe tube 542 applies a negative pressure on the tissue specimen to prevent the tissue specimen from exiting the needle 524 during extraction. After extraction, the tissue specimen may be discharged from the needle 524 by distally advancing the plunger 548 of the syringe 540.

Figure 21:
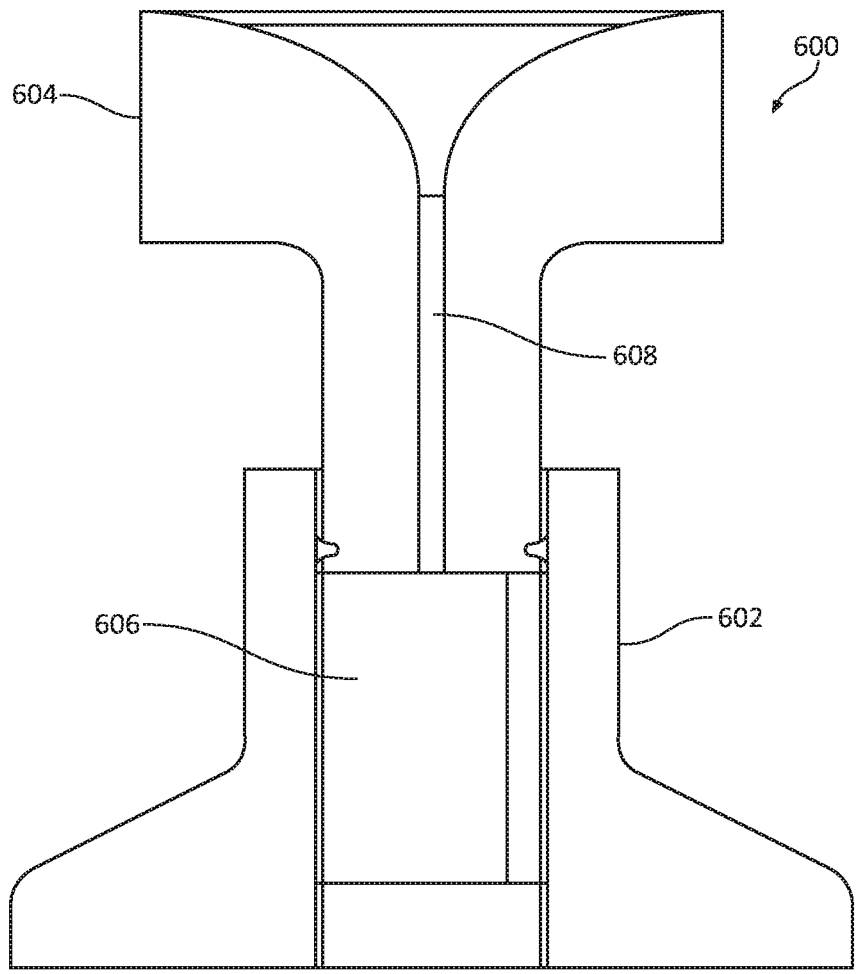
FIG. 21 is a front, cross-sectional view of a fluid station for use with any of the biopsy devices of the present disclosure.
Figure 22:
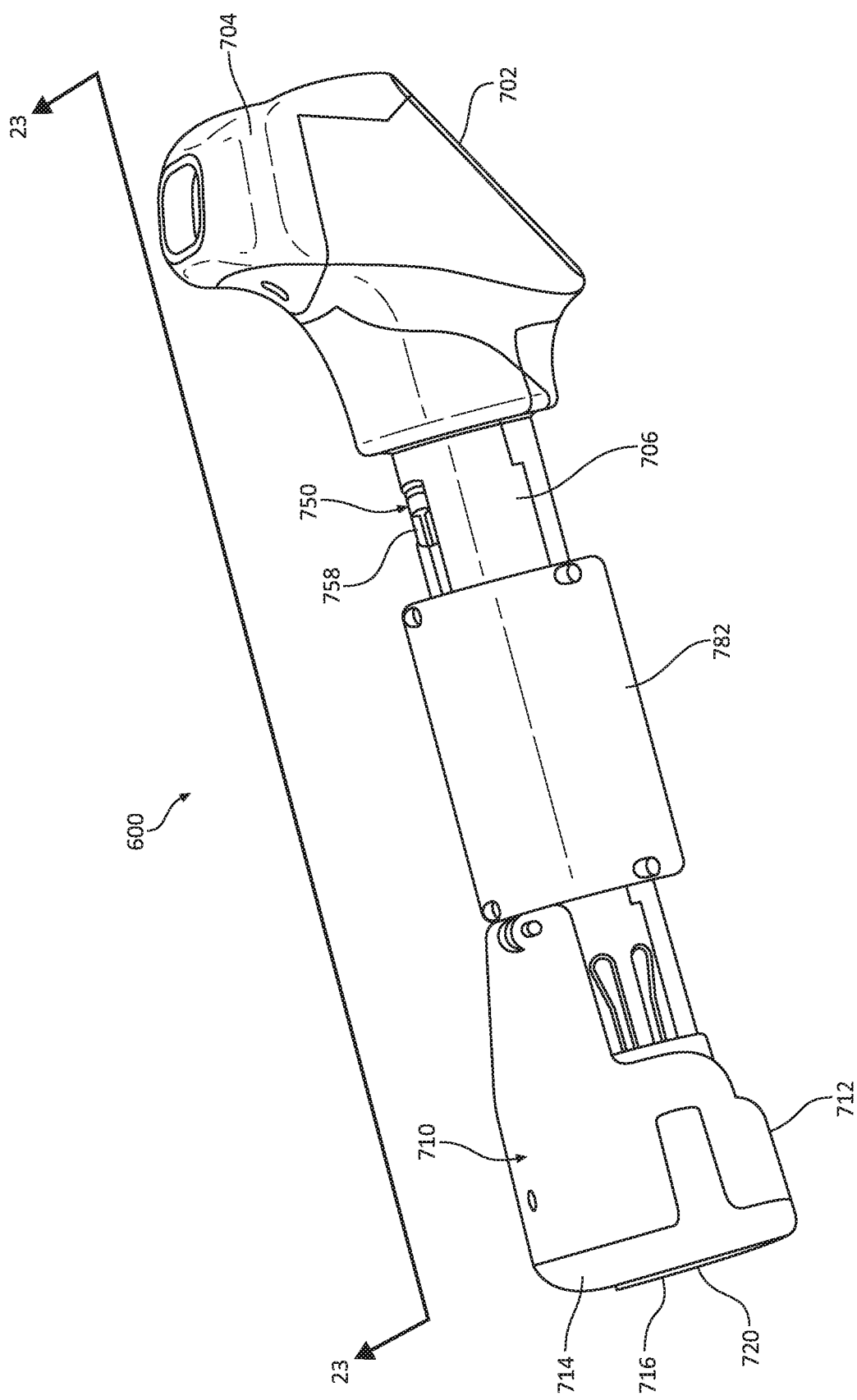
FIG. 22 is a perspective view of yet another embodiment of an ultrasonic biopsy device in accordance with the principles of the present disclosure.

With reference to FIG. 21, an external fluid station 600 may be provided which is configured to assist in extracting the tissue specimen from any of the biopsy devices described herein. The fluid station 600 includes a base 602 and a plunger 604. The base 602 defines an elongated channel 606 that contains a fluid therein. The plunger 604 defines a longitudinally-extending passageway 608 dimensioned for receipt of a needle of one of the disclosed biopsy devices. Upon positioning a needle in the passageway 608, a needle tip of the needle extends distally out of the plunger 604 and into the fluid contained in the base 602. To extract the tissue specimen from the needle, the plunger 604 is advanced distally relative to the base 602 to force the liquid through the needle tip. As the liquid is force up through the needle tip, the tissue specimen travels proximally through the needle and out of the biopsy device.

With reference to FIGS. 22-31, another embodiment of a biopsy device 700 is illustrated. The biopsy device 700 generally includes a display 702, an ultrasonic probe 710, and a needle assembly 760. The display 702 is disposed on a head 704 of the biopsy device 700 and is in electrical communication with the ultrasonic probe 710 such that any information sensed by the ultrasonic probe (e.g., tissue structure) is displayed on the display 702. The head 704 may include a processor in communication with the display 702 and the ultrasonic probe 710 for processing the information sensed by the ultrasonic probe 710.

With specific reference to FIGS. 22-26, the biopsy device 700 further includes a tubular shaft 706 extending distally from the head 704. In embodiments, the tubular shaft 706 may be monolithically formed with or integrally connected to the head 704. The tubular shaft 706 has a needle housing 708 fixed to a distal end portion thereof. The needle housing 708 includes a pair of tabs or stops 709a, 709b extending laterally outward from opposite sides thereof.

Figure 26:
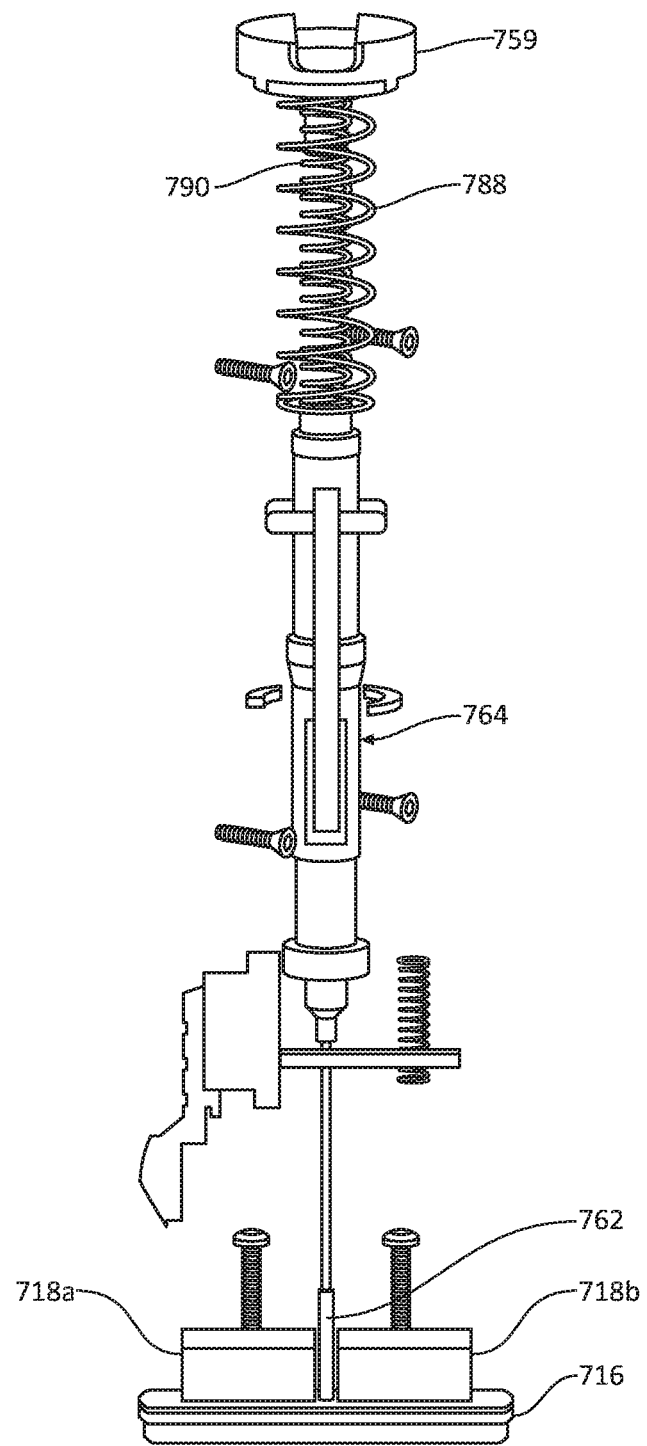
FIG. 26 is a front view, with some parts removed, of the ultrasonic biopsy device of FIG. 22.
Figure 27:
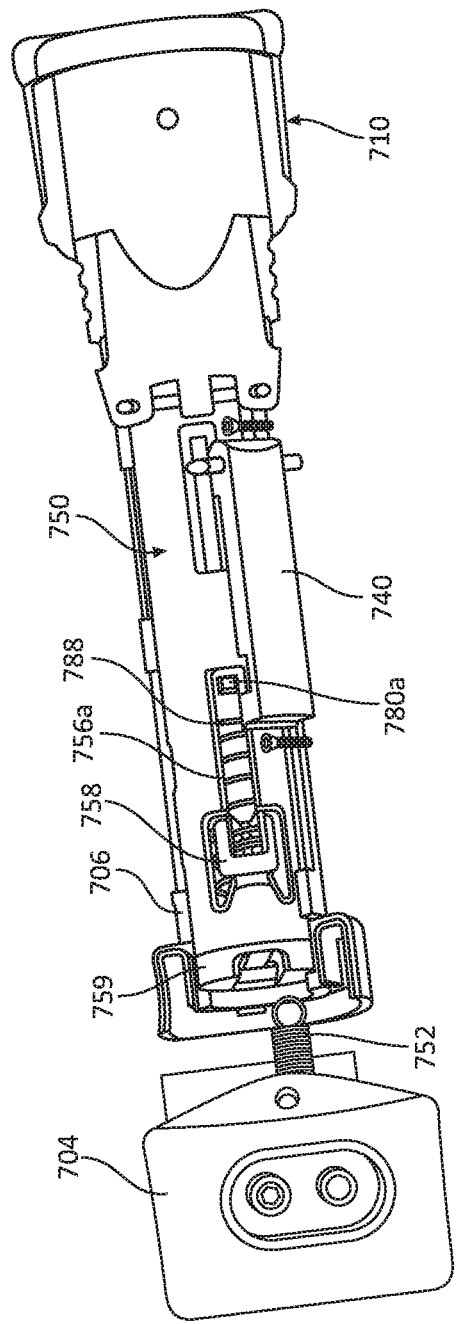
FIG. 27 is a perspective view, with some parts removed, of the ultrasonic biopsy device of FIG. 22.

The ultrasonic probe 710 includes a housing 712 pivotably coupled to the distal end portion of the tubular shaft 706 and an end cap 714 secured to the housing 712. The end cap 714 has a block 716 that supports a pair of ultrasonic sensors 718a, 718b (FIG. 26). The block 716 may be fabricated from silicone or any other suitable ultrasound-opaque material. The block 716 defines a central opening 720 therethrough dimensioned for slidable receipt of a needle 762 of the needle assembly 760. The ultrasonic sensors 718a, 718b are in communication with the processor and/or the display 702 and are laterally spaced from one another to accommodate the needle 762 of the needle assembly 762 therebetween. In this way, the needle 762 may be moved through the ultrasonic probe 710 without inhibiting its function.

Disposed within the tubular shaft 706 is an axially movable inner sheath 750. The inner sheath 750 is resiliently biased in a proximal direction by a biasing member 752 (e.g., an extension spring) that interconnects the inner sheath 750 and the head 704. The inner sheath 750 includes a pair of tabs or stops 754a, 754b located at a distal end portion thereof that matingly engage with the stops 709a, 709b of the needle housing 708 upon the inner sheath 750 moving from a proximal position (shown in FIG. 25) to a distal position (shown in FIG. 29). As such, when the inner sheath 750 is in the distal position, the inner sheath 750 is prevented from being retracted by the biasing member 752 toward the proximal position.

The inner sheath 750 defines a pair of longitudinally-extending channels 756a, 756b in an outer surface thereof. The channels 756a, 756b of the inner sheath 750 permit longitudinal movement of respective arms 780a, 780b of the needle assembly 760 therethrough. The inner sheath 750 includes a flexible locking member 758 located at a proximal end of one of the channels 756a, 756b. The locking member 758 of the inner sheath 750 is configured to releasably capture one of the arms 780a, 780b of the needle assembly 760 upon the needle assembly 760 entering a retracted position. The locking member 758 is adjacent an end of an actuator or trigger 740 (FIG. 27) of the biopsy device 700. The actuator 740 is pivotably coupled to the tubular shaft 706 and is configured to flex or bend the locking member 758 of the inner sheath 750 inwardly to selectively disengage the locking member 758 of the inner sheath 750 from the arm 780a of the needle assembly 760. As will be described in detail below, the inner sheath 750 functions to automatically retract the needle assembly 760 back to the retracted state after the needle assembly 760 is deployed.

The needle assembly 760 of the biopsy device 700 generally includes a needle subassembly 764 and the needle 762 extending distally from the needle subassembly 764. The needle subassembly 764 includes a pair of distally-extending legs 766a, 766b each having a ramped distal end 768a, 768b. The ramped distal ends 768a, 768b of the legs 766a, 766b are configured to engage with the stops 754a, 754b of the inner sheath 750 upon the needle assembly 760 moving distally into the deployed position. As will be described in greater detail below, as the ramped distal ends 768a, 768b of the legs 766a, 766b engage the respective stops 754a, 754b of the inner sheath 750, the stops 754a, 754b of the inner sheath 750 are forced radially outward and therefore out of engagement with the stops 709a, 709b of the needle housing 708.

The needle subassembly 764 further includes a pair of arms 780a 780b extending radially outward of the inner sheath 750. The arms 780a, 780b are coupled to a collar or slider 782 that is slidably attached to the tubular shaft 706 such that axial movement of the collar 782 along the elongated shaft 706 causes axial movement of the needle assembly 760. The collar 782 defines a pair of longitudinal tracks 784a, 784b therealong and a pair of circumferential notches 786a, 786b (FIG. 28) therein. The longitudinal tracks 784a, 784b and the circumferential notches 786a, 786b are each configured for selective receipt of the arms 780a, 780b of the needle subassembly 764. In one instance, when the arms 780a, 780b of the needle subassembly 764 are received in the respective tracks 784a, 784b of the collar 782, the needle subassembly 764 is axially movable through the tracks 784a, 784b and relative to the collar 782. In another instance, when the arms 780a, 780b of the needle subassembly 764 are received within the respective notches 786a, 786b (FIG. 28) defined in the collar 782 (due to a rotation of the collar 782), axial movement of the collar 782 causes the needle subassembly 764 to move with the collar 782.

The biopsy device 700 includes a pair of needle actuators 788, 790 (e.g., springs) that extend between a proximal cap 759 of the inner sheath 750 and a proximal end of the needle subassembly 764. In some embodiments, the biopsy device 700 may include more or less than two needle actuators. The needle actuators 788, 790 resiliently bias the needle assembly 760 distally away from the proximal cap 759 of the inner sheath 750 toward a deployed position.

Figure 23:
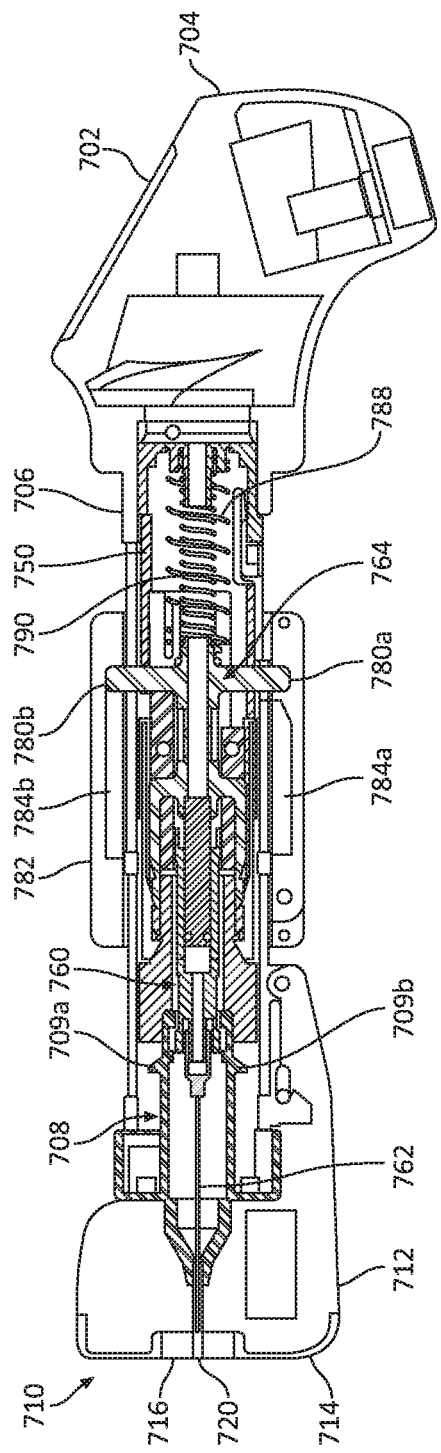
FIG. 23 is a cross-sectional view, taken alone line 23-23, of the ultrasonic biopsy device of FIG. 22.
Figure 24:
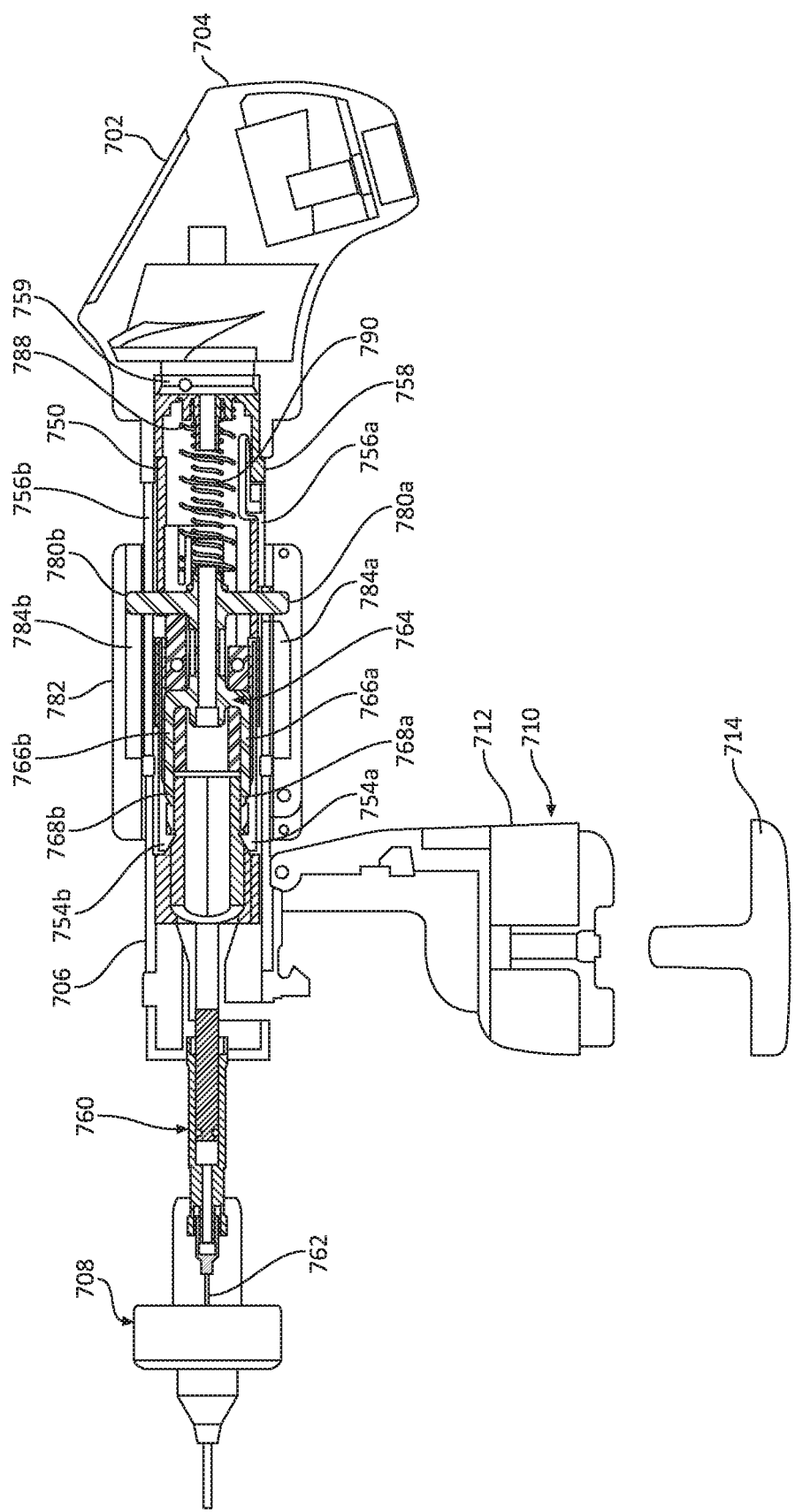
FIG. 24 illustrates the ultrasonic biopsy device of FIG. 23 in a disassembled state.
Figure 25:
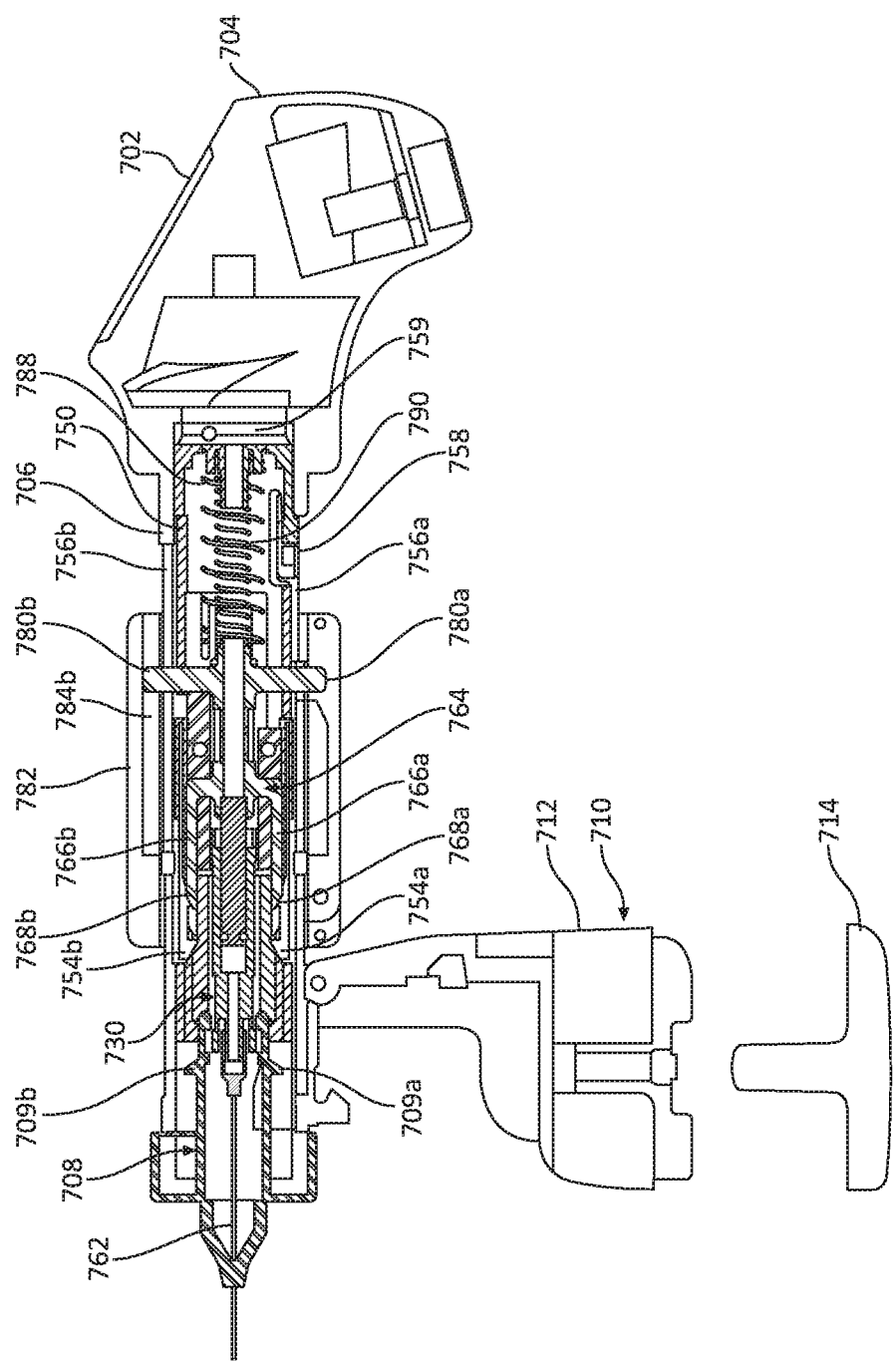
FIG. 25 illustrates the ultrasonic biopsy device of FIG. 23 in a partially disassembled state.

An exemplary use of the biopsy device 700 will now be described with reference to FIGS. 23 and 28-31. The biopsy device 700 may be used to extract tissue samples from a lesion, for example, a tumor to be tested. With the needle 762 disposed within needle housing 708 in a position proximal to opening 720 in the ultrasonic probe 710, as shown in FIG. 23, the biopsy device 700 is positioned such that the block 716 of the ultrasonic probe 710 is in abutting engagement with an outer surface of tissue (e.g., breast tissue). The ultrasonic sensors 718a, 718b (FIG. 26) of the ultrasonic probe 710 are activated to emit an ultrasonic field in a distal direction through the block 716 and toward the lesion. The ultrasonic sensors 718a, 718b then receive the reflected sound waves and the processor of the biopsy device 700 generates an image of the needle tip of the needle 762 and the lesion on the display 702. The biopsy device 700 is moved relative to the target tissue until the needle tip is shown on the display 702 as being aligned with the target tissue.

Figure 28:
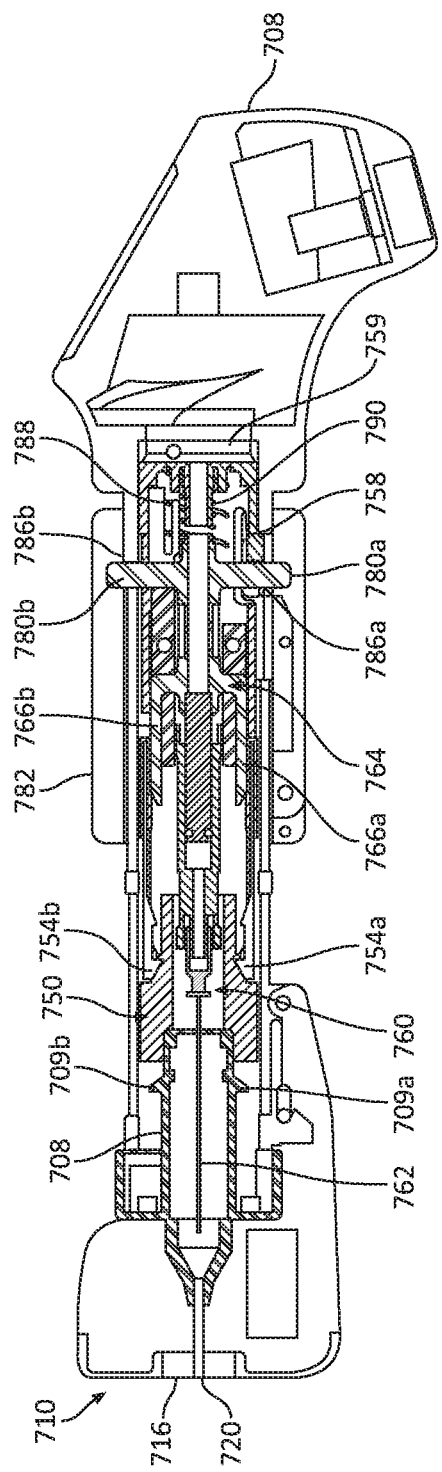
FIG. 28 illustrates the ultrasonic biopsy device of FIG. 23 in a first pre-firing state.

With reference to FIGS. 23 and 28, with the needle 762 in the proper position, the biopsy device 700 may be cocked in preparation for firing the needle assembly 760. To cock or set the needle assembly 760, the collar 782 is rotated relative to the arms 780a, 780b of the needle subassembly 764 to position the arms 780a, 780b of the needle assembly 764 in the notches 786a, 786b of the collar 782. With the arms 780a, 780b of the needle subassembly 764 captured in the notches 786a, 786b of the collar 782, proximal movement of the collar 782 along the tubular shaft 706 results in a retraction of the needle assembly 760 toward the proximal cap 759 of the inner sheath 750. Upon the needle subassembly 764 engaging the proximal cap 759 of the inner sheath 750, one of the arms 780a, 780b of the needle subassembly 764 is received in the flexible locking member 758 of the inner sheath 750 to lock together the needle assembly 760 and the inner sheath 750, as shown in FIG. 28. In addition to locking the needle assembly 760 with the inner sheath 750, proximal retraction of the needle assembly 760 within the tubular shaft 706 acts to compress the needle actuators 788, 790 between the needle subassembly 764 and the proximal cap 759 of the inner sheath 750.

Figure 29:
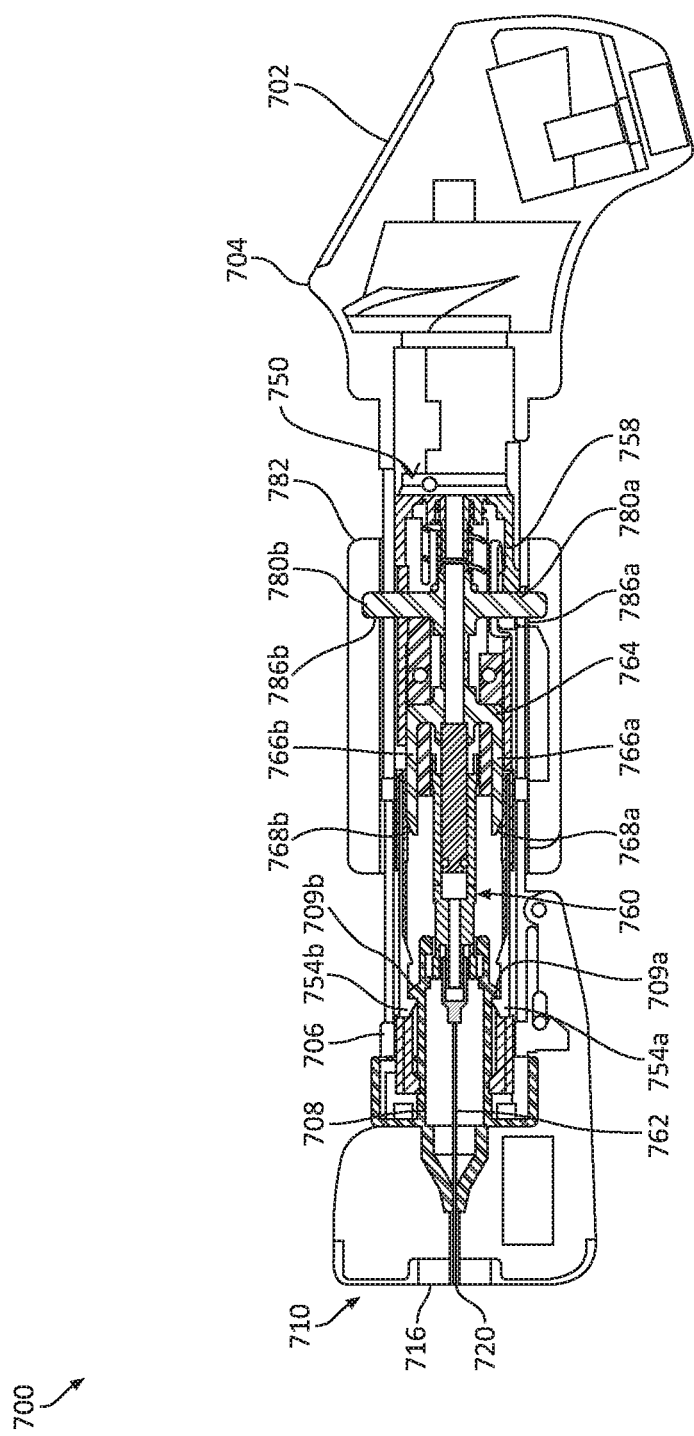
FIG. 29 illustrates the ultrasonic biopsy device of FIG. 23 in a second pre-firing state.

To further prepare the biopsy device 700 for firing, the collar 782 is advanced distally along the elongated shaft 706, which, in turn, drives distal advancement of the needle assembly 760 due to the arms 780a, 780b of the needle assembly 764 being captured in the notches 786a, 786b of the collar 782. As a result of arms 780a of the needle assembly 764 being in locking engagement with the locking member 758 of the inner sheath 750, as the needle assembly 760 moves distally the inner sheath 750 follows. As the inner sheath 750 moves toward a distal position within the tubular shaft 706, the stops 754a, 754b of the inner sheath 750 pass over and interlock with the stops 709a, 709b of the needle housing 708, as shown in FIG. 29. Since the needle housing 708 is fixed relative to the tubular shaft 706, the proximally-oriented force applied to the inner sheath 750 by the biasing member 752 (FIG. 27) will not result in proximal movement of the inner sheath 750 back toward the retracted position. As such, the collar 782, the needle assembly 760, and the inner sheath 750 are each prevented from moving proximally out of the position shown in FIG. 29. In this pre-fired position, the needle 762 is held within the opening 720 defined in the block 716 of the ultrasonic transducer 710 without protruding distally from the ultrasonic probe 710.

Figure 30:
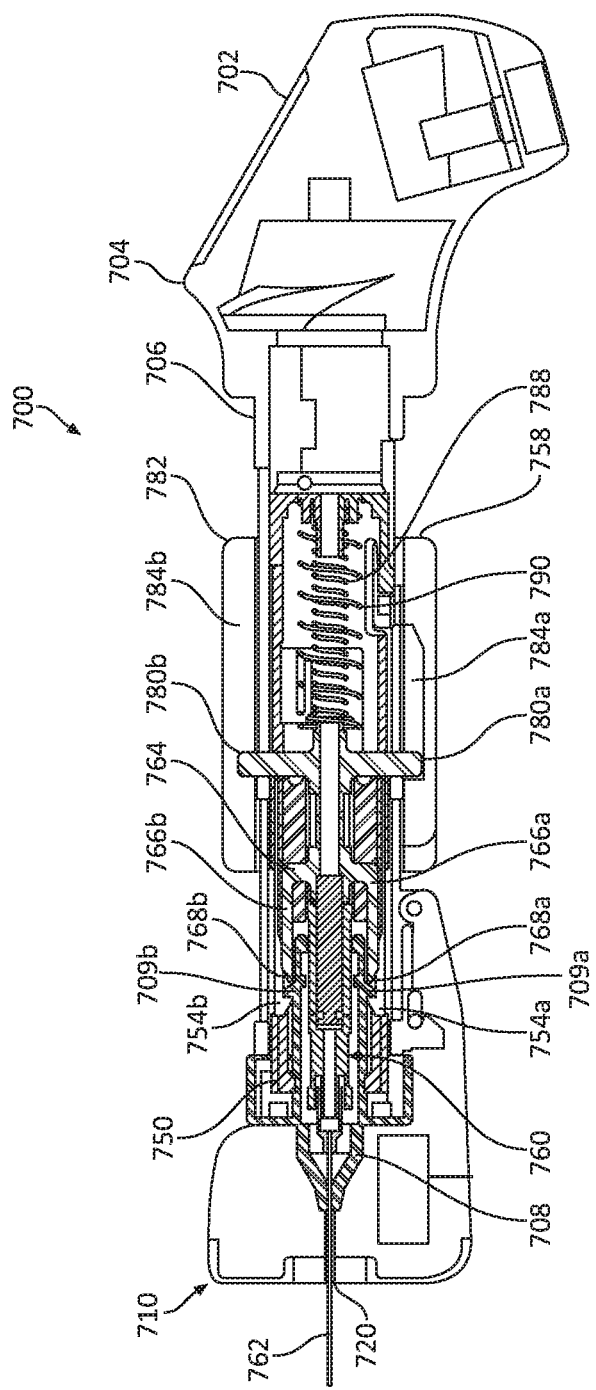
FIG. 30 illustrates the ultrasonic biopsy device of FIG. 23 in a fired state.

With reference to FIGS. 29 and 30, prior to firing the actuator 740 (FIG. 27), the collar 782 is rotated to displace the arms 780a, 780b of the needle subassembly 764 out of the notches 786a, 786b of the collar 782 and into the longitudinal tracks 784a, 784b of the collar 782. As can be appreciated by viewing, for example, FIG. 30, the collar 782 is prevented from moving distally relative to and along the elongated shaft 706 by virtue of an abutting engagement with the housing 712 of the ultrasonic probe 710. As such, the collar 782 acts as a safety by preventing distal movement of the needle assembly 760 relative thereto due to the arms 780a, 780b of the needle subassembly 764 being captured within the notches 786a, 786b of the collar 782. Prior to rotating the collar 782, incidental firing of the actuator 740 (FIG. 27) will not result in the firing of the needle assembly 760.

With the arms 780a, 780b of the needle subassembly 764 disposed within the tracks 784a, 784b of the collar 782, the needle assembly 760 is free to move distally along and relative to the collar 782 but for the locking engagement of the locking member 758 of the inner sheath 750 with the arm 780a of the needle subassembly 764. To deploy the needle assembly 760, the actuator 740 (FIG. 27) is pivoted into engagement with the locking member 758 of the inner sheath 750, which, in turn, moves the locking member 758 of the inner sheath 750 out of locking engagement with the arm 780a of the needle subassembly 764. With the arm 780a of the needle subassembly 764 released from the locking member 758 of the inner sheath 750, the needle actuator 788 is free to push the needle assembly 760 distally relative to the inner sheath 750 to deploy the needle 762 through and distally beyond the ultrasonic transducer 710 and into tissue. The second needle actuator 790 either occludes the proximal end of the needle assembly to create a passive vacuum or pushes the outer sheath of the side-biting needle over the inner core.

Figure 31:
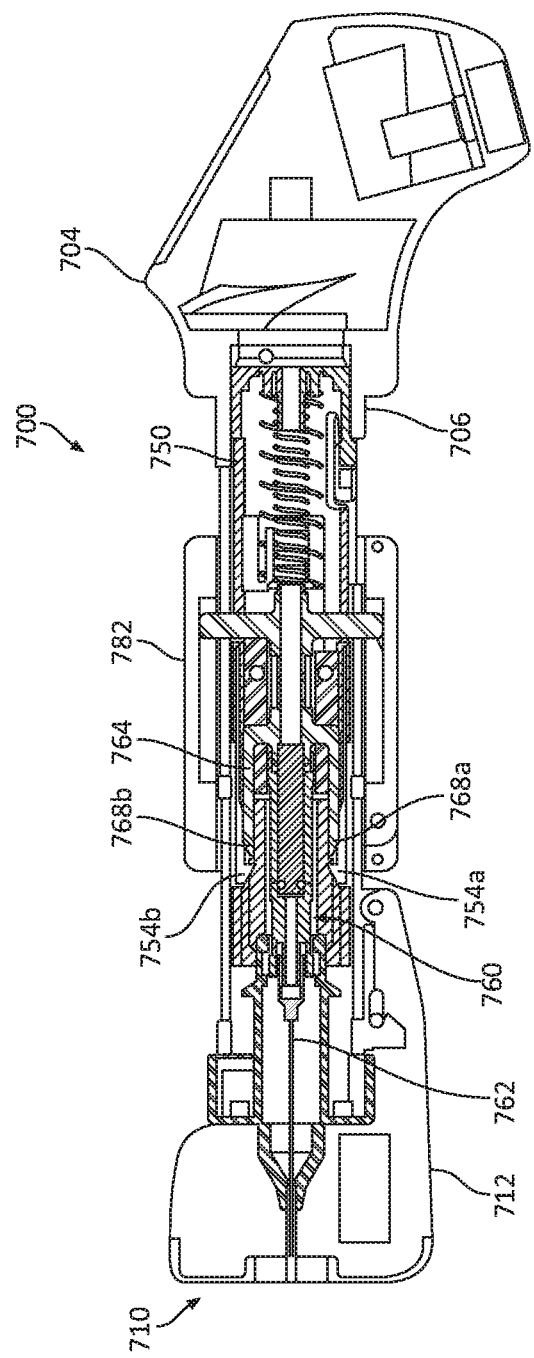
FIG. 31 illustrates the ultrasonic biopsy device of FIG. 23 in a post-fired state.

As the needle assembly 760 completes its deployment, the ramped distal ends 768a, 768b of the legs 766a, 766b of the needle subassembly 764 concurrently depress the stops 709a, 709b of the needle housing 708 thereby releasing the stops 754a, 754b of the inner sheath 750 from the stops 709a, 709b of the needle housing 708. Upon release of the inner sheath 750 from the needle housing 708, the biasing member 752 (FIG. 27) in the head 704 drives the inner sheath 750 proximally toward the retracted position (as shown in FIG. 31). Proximal movement of the inner sheath 750 causes the needle assembly 760 to be retracted due to the engagement of the stops 754a, 754b of the inner sheath 750 and the ramped distal ends 768a, 768b of the needle subassembly 764. In this way, the needle 762 is immediately and automatically retracted back into the housing 712 of the ultrasonic probe 710 upon finishing its deployment. With tissue captured in the needle 762, a proximal end of the needle subassembly 764 is occluded by the movement driven by actuator 790, thereby creating a passive vacuum in the needle subassembly 764 to hold the tissue sample in the lumen of the needle 762. In embodiments, the tissue may be captured by forming an active vacuum from a plunger (not shown) activated as the needle 762 is retracted back into the housing 712. Needle actuator 752 retracts the inner sheath 750 and all components within it until the needle is completely enclosed behind the distal end of the ultrasound probe.

To remove the needle 762 from the needle subassembly 764, the ultrasonic probe 710 may be pivoted relative to the tubular shaft 706 to allow a clinician to gain access to the needle housing 708. The needle housing 708 may then be detached from the tubular shaft 706 by, e.g., unscrewing it from the distal end portion of the tubular shaft 706. With the needle housing 708 detached from the tubular shaft 706, the needle 762 is accessible by a clinician and may be removed from the biopsy device 700. With the needle 762 removed, the tissue sample may be extracted from the needle 762 and a new, sterile needle may be loaded into the biopsy device 700 in preparation of reuse of the biopsy device 700.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A biopsy device, comprising:
    a head;
    an elongated shaft extending distally from the head;
    an ultrasonic probe coupled to a distal end portion of the elongated shaft and having a channel defined therein;
    a display disposed on the head and in electrical communication with the ultrasonic probe, the ultrasonic probe configured to send a signal to the display to generate an image on the display;
    a needle assembly at least partially disposed within the elongated shaft, wherein the needle assembly is configured to move in a distal direction relative to the ultrasonic probe and through the channel of the ultrasonic probe from a retracted position to a deployed position;
    a first biasing member configured to move the needle assembly to the deployed position;
    a second biasing member configured to automatically retract the needle assembly after the needle assembly moves to the deployed position;
    a collar disposed about the elongated shaft and configured to move axially along and relative to the elongated shaft, wherein the collar is rotatable relative to the elongated shaft between a first orientation, in which the collar and the needle assembly are axially movable with one another, and a second orientation, in which the needle assembly is axially movable relative to the collar.

2. The biopsy device according to claim 1, wherein the ultrasonic probe includes a longitudinal axis defined therealong, the ultrasonic probe configured to emit ultrasonic waves along the longitudinal axis such that the movement of the needle assembly from the retracted position toward the deployed position aligns with the ultrasonic waves.

3. The biopsy device according to claim 2, wherein the ultrasonic probe is configured to send signals to the display corresponding to a position of a needle of the needle assembly to generate the image on the display of the position of the needle of the needle assembly.

4. The biopsy device according to claim 3, wherein the display is configured to display a projected needle pathway of the needle.

5. The biopsy device according to claim 1, wherein the needle assembly includes a hub and a needle extending distally from the hub, the needle defining a longitudinal axis.

6. The biopsy device according to claim 1, wherein the needle assembly includes:
    a body that defines a chamber therein; and
    a needle extending distally from the body.

7. The biopsy device according to claim 6, further comprising a tube extending alongside the needle.

8. The biopsy device according to claim 1, wherein the ultrasonic probe includes a distal cap defining a central opening having a needle of the needle assembly selectively extending therethrough.

9. The biopsy device according to claim 8, wherein the distal cap has a window for conducting ultrasound waves therethrough.

10. The biopsy device according to claim 1, wherein the needle assembly is configured to advance from the retracted position to an intermediate, pre-fired position, and from the intermediate, pre-fired position to the deployed position.

11. The biopsy device according to claim 1, wherein the collar defines a longitudinally-extending track and a notch in communication with the track, the needle assembly having an arm configured for receipt in the notch when the collar is in the first orientation and configured for receipt in the track when the collar is in the second orientation.

12. The biopsy device according to claim 11, further comprising a locking member configured to move between a first position, in which the locking member is lockingly engaged to the arm of the needle assembly to prevent advancement of the needle assembly, and a second position, in which the locking member releases the arm of the needle assembly to permit the needle assembly to move to the deployed position.

13. The biopsy device according to claim 12, wherein the first and second biasing members are each springs disposed between the needle assembly and the head.

14. The biopsy device according to claim 13, further comprising an inner sheath disposed within the elongated shaft and resiliently biased in a proximal direction by the second biasing member, wherein the inner sheath is configured to move the needle assembly from the deployed position to the retracted position.

15. The biopsy device according to claim 14, wherein the inner sheath defines a longitudinally-extending channel in an outer surface thereof configured for longitudinal translation of the arm of the needle assembly therethrough.

16. The biopsy device according to claim 15, wherein the locking member is axially fixed and pivotably coupled to the inner sheath and aligned with the channel of the inner sheath.

17. The biopsy device according to claim 15, wherein the needle assembly is configured to move relative to the inner sheath from the retracted position to the deployed position and is configured to be axially restrained to the inner sheath upon moving to the deployed position, such that the inner sheath and the needle assembly retract as one unit as the needle assembly moves from the deployed position to the retracted position.

18. The biopsy device according to claim 17, wherein the inner sheath is transitionable between a first state, in which the inner sheath is axially fixed relative to the elongated shaft, and a second state, in which the inner sheath is axially movable relative to the elongated shaft, wherein the needle assembly is configured to transition the inner sheath from the first state to the second state upon moving to the deployed position.

19. The biopsy device according to claim 1, further comprising:
    a needle housing coupled to the distal end portion of the elongated shaft and having a stop; and
    an inner sheath housing the needle assembly therein and having a tab, the second biasing member exerting a proximally-oriented, resilient bias on the inner sheath, the inner sheath being configured to move relative to the elongated shaft between a proximal position and a distal position, in which the tab of the inner sheath matingly engages the stop of the needle housing to prevent the inner sheath from moving proximally out of the proximal position, wherein the needle assembly has a leg configured to release the tab of the inner sheath from the stop of the needle housing and matingly engage the tab of the inner sheath upon the needle assembly moving to the deployed position, such that the inner sheath and the needle assembly automatically retract together as one unit via the second biasing member.

20. A biopsy device, comprising:

a head;

an elongated shaft extending distally from the head;

an ultrasonic probe coupled to a distal end portion of the elongated shaft and having a channel defined therein;

a display disposed on the head and in electrical communication with the ultrasonic probe, the ultrasonic probe configured to send a signal to the display to generate an image on the display;

a needle assembly at least partially disposed within the elongated shaft, wherein the needle assembly is configured to move in a distal direction relative to the ultrasonic probe and through the channel of the ultrasonic probe from a retracted position to a deployed position;

a first biasing member configured to move the needle assembly to the deployed position;

a second biasing member configured to automatically retract the needle assembly after the needle assembly moves to the deployed position;

a needle housing coupled to the distal end portion of the elongated shaft and having a stop; and an inner sheath housing the needle assembly therein and having a tab, the second biasing member exerting a proximally-oriented, resilient bias on the inner sheath, the inner sheath being configured to move relative to the elongated shaft between a proximal position and a distal position, in which the tab of the inner sheath matingly engages the stop of the needle housing to prevent the inner sheath from moving proximally out of the proximal position, wherein the needle assembly has a leg configured to release the tab of the inner sheath from the stop of the needle housing and matingly engage the tab of the inner sheath upon the needle assembly moving to the deployed position, such that the inner sheath and the needle assembly automatically retract together as one unit via the second biasing member.

\* \* \* \* \*